(12) United States Patent
Szillat et al.

(10) Patent No.: US 11,918,664 B2
(45) Date of Patent: Mar. 5, 2024

(54) DIRECT DENTAL FILLING COMPOSITIONS

(71) Applicant: DENTSPLY SIRONA inc., York, PA (US)

(72) Inventors: Florian Szillat, Neukirchen-Vluyn (DE); Caroline Renn, Singen (DE); Christoph Weber, Constance (DE); Uwe Walz, Constance (DE); Joachim Klee, Radolfzell (DE)

(73) Assignee: DENTSPLY SIRONA INC., York, PA (US)

(*) Notice: Subject to any disclaimer, the term of this patent is extended or adjusted under 35 U.S.C. 154(b) by 64 days.

(21) Appl. No.: 17/343,886

(22) Filed: Jun. 10, 2021

(65) Prior Publication Data

US 2021/0308019 A1    Oct. 7, 2021

Related U.S. Application Data

(63) Continuation of application No. 16/472,011, filed as application No. PCT/EP2017/082698 on Dec. 13, 2017, now Pat. No. 11,071,693.

(30) Foreign Application Priority Data

Dec. 20, 2016  (EP) .................... 16205373

(51) Int. Cl.
  *A61K 6/889* (2020.01)
  *C08K 5/14* (2006.01)
  *C08L 33/08* (2006.01)
  *C08L 33/10* (2006.01)
  *C08L 33/26* (2006.01)

(52) U.S. Cl.
  CPC ............. *A61K 6/889* (2020.01); *C08K 5/14* (2013.01); *C08L 33/08* (2013.01); *C08L 33/10* (2013.01); *C08L 33/26* (2013.01)

(58) Field of Classification Search
  None
  See application file for complete search history.

(56) References Cited

U.S. PATENT DOCUMENTS

| | | | |
|---|---|---|---|
| 3,655,605 A * | 4/1972 | Smith | C08K 3/22 106/35 |
| 3,814,717 A * | 6/1974 | Wilson et al. | A61K 6/887 106/35 |
| 4,089,830 A | 5/1978 | Tezuka | |
| 4,143,018 A * | 3/1979 | Crisp | A61K 6/889 524/833 |
| 4,209,434 A * | 6/1980 | Wilson | A61K 6/889 106/35 |
| 4,298,738 A | 11/1981 | Lechtken | |
| 4,317,681 A | 3/1982 | Beede | |
| 4,324,744 A | 4/1982 | Lechtken | |
| 4,360,605 A * | 11/1982 | Schmitt | A61K 6/889 524/559 |
| 4,374,936 A | 2/1983 | Tomioka | |
| 4,376,835 A * | 3/1983 | Schmitt | C03C 3/04 106/35 |
| 4,385,109 A | 5/1983 | Lechtken | |
| 4,814,362 A | 3/1989 | Billington | |
| 4,900,546 A * | 2/1990 | Posey-Dowty | A61L 24/001 623/23.62 |
| 5,130,347 A * | 7/1992 | Mitra | A61K 6/62 523/117 |
| 5,154,762 A | 10/1992 | Mitra | |
| 5,318,929 A | 6/1994 | Jana | |
| 5,360,770 A | 11/1994 | Chadwick | |
| 5,501,727 A | 3/1996 | Wang | |
| 10,610,462 B2 * | 4/2020 | Renn | A61K 6/889 |
| 11,071,693 B2 * | 7/2021 | Florian | C08L 33/26 |
| 2002/0010227 A1 * | 1/2002 | Culbertson | C08F 8/30 524/808 |
| 2004/0079258 A1 | 4/2004 | Hoescheler | |
| 2004/0157954 A1 * | 8/2004 | Imai | A61L 24/06 523/115 |
| 2005/0165136 A1 * | 7/2005 | Mays | A61K 6/20 524/556 |
| 2005/0252413 A1 * | 11/2005 | Kangas | A61K 6/30 106/35 |
| 2009/0105144 A1 * | 4/2009 | Vogt | A61L 24/0089 525/50 |
| 2009/0105367 A1 * | 4/2009 | Vogt | A61L 27/26 252/182.15 |
| 2009/0105369 A1 * | 4/2009 | Vogt | A61L 24/043 523/116 |
| 2010/0228358 A1 * | 9/2010 | Leonard | A61L 24/0073 623/23.62 |
| 2010/0329074 A1 * | 12/2010 | Vogt | B01F 31/441 366/190 |
| 2012/0016094 A1 * | 1/2012 | Takei | A61K 6/30 526/181 |
| 2013/0289216 A1 * | 10/2013 | Klee | A61K 6/889 525/296 |
| 2014/0228474 A1 * | 8/2014 | Qian | A61K 6/77 523/116 |
| 2016/0256362 A1 * | 9/2016 | Skaria | C09J 4/00 |
| 2018/0237567 A1 * | 8/2018 | Klee | C07C 233/20 |

(Continued)

FOREIGN PATENT DOCUMENTS

CN    1394567 A    2/2003
CN    103270055 A  8/2013

(Continued)

OTHER PUBLICATIONS

HEMA OECD SIDS (Year: 2001).*

(Continued)

*Primary Examiner* — Peter A Salamon
(74) *Attorney, Agent, or Firm* — DENTSPLY SIRONA INC.

(57) ABSTRACT

The present invention relates to an aqueous dental glass ionomer composition for use in the treatment of cavitated carious lesions, which composition comprises a water-soluble, polymerizable polymer comprising acidic groups, which is reactive with the particulate glass in a cement reaction, whereby the polymerizable polymer has a polymer backbone and pendant groups having one or more polymerizable carbon-carbon double bonds. The dental glass ionomer composition is used as a permanent direct restoration.

13 Claims, No Drawings

(56) References Cited

U.S. PATENT DOCUMENTS

2018/0353391 A1* 12/2018 Renn .................. A61K 6/889
2019/0343730 A1* 11/2019 Florian ................ C08L 33/26

FOREIGN PATENT DOCUMENTS

| EP | 0173567 | A2 | 3/1986 | | |
|----|---------|----|--------|---|---|
| EP | 0969789 | A2 | 1/2000 | | |
| EP | 2604247 | A1 | 6/2013 | | |
| EP | 2705827 | A1 | 3/2014 | | |
| JP | 2014501821 | A | 1/2014 | | |
| WO | 9917716 | A2 | 4/1999 | | |
| WO | WO-03011232 | A1 * | 2/2003 | ........... | A61K 6/0835 |
| WO | 2014040729 | A1 | 3/2014 | | |

OTHER PUBLICATIONS

Chen et al.; Phase Behavior and Self-Assembly of Poly [N-vinylformamide-co-(acrylic acid)] Copolymers Under Highly Acidic Conditions; Journal of Applied Polymer Science; vol. 109 (2008); pp. 2802-2807.

Nesterova et al.; Radical Copolymerization of N-Vinylformamide with Unsaturated Carboxylic Acids; Russian Journal of Applied Chemistry; vol. 82, No. 4 (2009); pp. 618-621.

* cited by examiner

DIRECT DENTAL FILLING COMPOSITIONS

THE CROSS-REFERENCE TO RELATED APPLICATIONS

This patent application is continuation of application Ser. No. 16/472,011, filed on Jun. 20, 2019, published as US 2019/0343730 and now issued as U.S. Pat. No. 11,071,693, which is a national phase of PCT/EP2017/082698, filed Dec. 13, 2017, which claims the benefit of and priority to European Patent Application No. 16205373.0, filed on Dec. 20, 2016, which is herein incorporated by reference for all purposes.

FIELD OF THE INVENTION

The present invention relates to a dental filling material for use as a permanent, stress bearing dental restorative material. Specifically, the present invention relates to an aqueous dental glass ionomer composition for use as a permanent direct restoration in the treatment of deep cavitated carious lesions.

BACKGROUND OF THE INVENTION

Carious lesions develop when bacteria in the mouth release acids that demineralize and soften the tooth surface. Initially white spot lesions of demineralized enamel are formed. If the demineralization process is not interrupted or reversed, carious lesions progress further into the tooth structure and form cavities. Ultimately, untreated caries lead to infection and tooth loss.

A range of options is available to restore the decayed tooth's structure by a direct restoration which is placed as malleable filling material and subsequently hardens. Depending on the choice of filling material, liners need to be used to protect the pulp, or the use of enamel etching, adhesives, and light curing may be required.

In general, direct filling materials are required to have good mechanical properties including preferably adhesive properties to hard dental tissue, high biocompatibility, and sufficient mechanical and chemical resistance over an extended period of time given the harsh conditions for a restorative material in the buccal cavity. Moreover, dental restorative materials should have good handling properties and should not be sensitive to variations in the treatment conditions or application technique. Moreover, inexpensive dental restorative materials are often preferred.

Direct filling materials can be categorized as non-aesthetic or aesthetic. Non-aesthetic filling materials typically include amalgam. Aesthetic restorations typically include dental composites or glass ionomer cements.

Amalgam is perceived to provide dental professionals with a strong, well-retained, and cost-effective option. However, amalgam is also considered to be undesirable for reasons of toxicological concerns.

Dental composite materials rely on the radical polymerization of a polymerizable organic matrix containing a dental filler, and have excellent mechanical properties including a flexural strength of typically greater than 80 MPa. Moreover, dental composite materials resemble the natural colour of teeth. However, dental composite materials are more expensive to produce than amalgam, and require more time and greater expertise to fit, in particular for ensuring moisture control.

Glass ionomer cements containing a reactive glass powder, a polyalkenoic acid and water show adhesion to hard dental tissue and excellent biocompatibility. Moreover, glass ionomer cements provide good chemical resistance in the buccal cavity over an extended period of time. Glass ionomer cements have excellent handling properties and do not require complicated application or curing steps. Also, variations in the application conditions as well as in the application technique usually do not have much impact on the success of the treatment. Dental glass ionomer cements are inexpensive. Finally, fluoride releasing dental glass ionomer cements provide cariostatic properties.

However, conventional glass ionomer cements have a low flexural strength of usually less than 40 MPa and are brittle due to salt-like structures formed by the acid-base reaction between the reactive glass powder and the polyalkenoic acid when the glass is cured.

The mechanical properties of glass ionomer cements may be improved by the selection of a functionalized polyacidic polymer.

Chen et al. and Nesterova et al. (Chen et al., J. Appl. Polym. Sci., 109 (2008) 2802-2807; Nesterova et al., Russian Journal of Applied Chemistry, 82 (2009) 618-621) disclose copolymers of N-vinylformamide with acrylic acid and/or methacrylic acid, respectively.

Moreover, a polymer having polymerizable moieties as pendant groups can be crosslinked in order to increase the mechanical resistance of the resulting glass ionomer cement.

For example, WO2003/011232 A1 discloses a polymerizable water-based dental glass ionomer cement containing two different polyacidic polymers. One of the polymers has a pendant post-polymerizable moiety linked to the polymer through an ester bond which is, however, prone to hydrolytic cleavage in acidic media.

WO2012/084206 A1 discloses a polymer for a dental glass ionomer cement. However, WO2012/084206 does not disclose a specific combination of components for a composition of a dental glass ionomer cement.

Conventional glass ionomer cements may be used for bonding indirect restorations such as inlays, onlays, crowns, bridges and veneers to hard dental tissue, provided that the indirect restoration shields the hardened dental glass ionomer cement from any excessive mechanical stress.

Conventional glass ionomer cements may also be used for the preparation of temporary direct restorations in non-stress bearing sites.

However, conventional dental glass ionomer cements cannot be used as a permanent direct restoration in the treatment of cavitated carious lesions since the cured cements will fail under high mechanical stress such as in particular in case the carious lesions are Class I, II, IV, V or VI.

Therefore, amalgam or dental composite materials are conventionally used as direct restorations in the treatment of cavitated carious lesions including Class I, II, and V carious lesions.

US-A 2005/165136 discloses ionomeric cements useful in dental and orthopedic medicine. According to Table 4 of the document, the light cured ionomeric cements show a flexural strength which is up to 5% higher than the flexural strength of Vitremer® light cured glass ionomer (3M Dental product) under the test conditions used according to US-A 2005/165136.

WO-A 2012/084206 discloses a polymer for a dental glass ionomer cements.

SUMMARY OF THE INVENTION

It is an object of the present invention to provide a direct dental filling material for use as a permanent, stress bearing dental restorative material, which may be used as a permanent direct restoration in the treatment of deep cavitated carious lesions.

The present invention provides an aqueous dental glass ionomer composition for use in the treatment of cavitated carious lesions, wherein the glass ionomer composition comprises
- (A) a reactive particulate glass,
- (B) a water-soluble, polymerizable polymer comprising acidic groups, which is reactive with the particulate glass in a cement reaction, whereby the polymerizable polymer has a polymer backbone and pendant groups having one or more polymerizable carbon-carbon double bonds,
- (C) a polymerization initiator system;
- wherein the dental glass ionomer composition is used as a permanent direct restoration.

The present invention is based on the recognition that an aqueous dental glass ionomer composition may provide a hardened direct dental restoration having a flexural strength of at least 80 MPa. The present invention is further based on the recognition that a combination of a reactive particulate glass according to (A), a specific water-soluble, polymerizable polymer according to (B) and a polymerization initiator system according to (C) in an aqueous dental glass ionomer composition is required for providing a hardened direct dental restoration having a flexural strength of at least 80 MPa. Finally, the present invention is based on the recognition that an aqueous dental glass ionomer composition having a flexural strength of at least 80 MPa is suitable for use as a permanent, stress bearing restorative material, notably as a permanent direct restoration in the treatment of deep cavitated carious lesions.

DETAILED DESCRIPTION OF PREFERRED EMBODIMENTS

The term "(co)polymerizable" refers to compounds capable of combining by covalent bonding in an addition polymerization reaction to form a polymer. A "polymerizable polymer" may be combined with a crosslinker as well as with a hydrolysis-stable, water-soluble monomer having "polymerizable (carbon-carbon) double bond" respectively to form graft polymers and/or crosslinked polymers when curing the aqueous dental glass ionomer composition.

The terms "first polymerizable organic moiety", "second polymerizable organic moiety", "polymerizable pendant groups" and "polymerizable (carbon-carbon) double bond" as used herein in connection with component (B), and components (D) and (E) as defined below, of the present aqueous dental glass ionomer composition mean any double bond capable of addition polymerization, in particular free radical polymerization, preferably a carbon-carbon double bond.

The term "curing" includes the polymerization of functional monomers, oligomers and even polymers into a polymer network, in particular the polymerization of unsaturated monomers or oligomers in the presence of crosslinking agents.

The term "curable" refers to an aqueous dental glass ionomer composition that will polymerize into a crosslinked polymer network when irradiated for example with actinic radiation such as ultraviolet (UV), visible, or infrared radiation, or when reacted with polymerisation initiators.

The present aqueous dental glass ionomer composition provides a cured dental glass-ionomer composition based on a cement reaction of the basic particulate glass and the polyacid, and a free radical polymerization of a polymerizable polymer according to (B) and optional further polymerizable compounds, which free radical polymerization is initiated by a polymerization initiator system according to (C).

The Treatment of Cavitated Carious Lesions

The present aqueous dental glass ionomer composition is used in the treatment of cavitated carious lesions as a permanent direct restoration.

The treatment of carious lesions may be a conventional treatment approach in which all soft and leathery dentin is removed from the carious lesions until hard dentin is reached, before the final direct restoration is placed. For this conventional treatment approach, typically a dental drilling device is used. However, in case the carious lesions are deep and cavitated, thereby posing a risk of pulp exposure having detrimental effects on the treated tooth an incomplete carious removal technique may be applied. For example, an atraumatic restorative treatment (ART) approach in which only soft, infected dentine is removed manually using dental hand instruments may be considered. Accordingly, the resultant cavities are smaller compared to a conventional treatment approach using a dental drilling device.

Caries lesions may be classified according to the severity of the lesion. Accordingly, carious lesions may be moderate, advanced and severe carious lesions. Moderate carious lesions extend more than halfway through enamel, but do not involve the dentino-enamel junction (DEJ). Advanced carious lesions extend to or through the DEJ, but do not extend more than half the distance to the pulp (*Caries Profunda*). Severe carious lesions extend through enamel, through dentin, and more than half the distance to the pulp (*Caries Profunda complicata*).

Preferably, the present aqueous dental glass ionomer composition is used in the treatment of cavitated lesions, wherein the carious lesions are moderate, advanced or severe carious lesions, more preferably advanced or severe carious lesions.

Carious lesions may be classified depending on their location according to the classification established by G. V. Black, which distinguishes between the following classes I to VI:
- Class I: Cavity in pits or fissures on the occlusal surfaces of molars and premolars; facial and lingual surfaces of molars; lingual surfaces of maxillary incisors. Class I corresponds to surfaces of a posterior tooth one can clinically see occlusal/lingual/buccal surfaces. Therefore, the interproximal surfaces are not classified as Class I;
- Class II: Cavity on proximal surfaces of premolars and molars;
- Class III: Cavity on proximal surfaces of incisors and canines that do not involve the incisal angle;
- Class IV: Cavity on proximal surfaces of incisors or canines that involve the incisal angle. Class IV lesion is the larger version of Class III that covers the incisal angle:
- Class V: Cavity on the cervical third of the facial or lingual surfaces of any tooth, e.g. the neck of the tooth;
- Class VI: Cavity on incisal edges of anterior teeth and cusp tips of posterior teeth. Class VI corresponds to the very top surface of a tooth.

Preferably, the present aqueous dental glass ionomer composition is used in the treatment of cavitated lesions, wherein the carious lesions are Class I, II, IV, V or VI carious lesions.

(A) The Reactive Particulate Glass

The term "reactive particulate glass" refers to a solid mixture of mainly metal oxides transformed by a thermal melt process into a glass and crushed by various processes, which glass is capable of reacting with a polymer containing acidic groups in a cement reaction. The glass is in particulate form. Moreover, the reactive particulate glass may be surface modified, e.g. by silanation or acid treatment. Any conventional reactive dental glass may be used for the purpose of the present invention. Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable particulate reactive glasses may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

Preferably, the reactive particulate glass according to (A) is a reactive particulate glass comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The aqueous dental glass ionomer composition according to the present invention preferably comprises 20 to 90 percent by weight of the reactive particulate glass, more preferably 30 to 80 percent by weight, based on the total weight of the composition.

The reactive particulate glass usually has an average particle size of from 0.005 to 100 μm, preferably of from 0.01 to 40 μm as measured, for example, by electron microscopy or by using a conventional laser diffraction particle sizing method as embodied by a MALVERN Mastersizer S or MALVERN Mastersizer 2000 apparatus.

The reactive particulate glass may have a unimodal or multimodal (e.g., bimodal) particle size distribution, wherein a multimodal reactive particulate glass represents a mixture of two or more particulate fractions having different average particle sizes.

The reactive particulate glass may be an agglomerated reactive particulate glass which is obtainable by agglomerating a reactive particulate glass in the presence of a modified polyacid and/or polymerizable (meth)acrylate resins. The particle size of the agglomerated reactive particulate glass may be adjusted by suitable size-reduction processes such as milling.

The reactive particulate glass may be surface modified by using a component according to (B) or (C). In particular, the reactive particulate glass may be surface modified by using one or more components of the polymerization initiator system (C) in order to avoid contact of the one or more components of the polymerization initiator system (C) with an acid under aqueous conditions.

The reactive particulate glass may alternatively or additionally be surface modified by a surface modifying agent. Preferably, the surface modifying agent is a silane. A silane provides a suitable hydrophobicity to the reactive particulate glass, which allows for an advantageous, homogeneous admixture with the organic components according to (B), (C) and (D) of the aqueous dental glass ionomer composition.

(B) The Water-Soluble, Polymerizable Polymer Comprising Acidic Groups

The aqueous dental glass ionomer composition according to the invention comprises (B) a water-soluble, polymerizable polymer comprising acidic groups, which is reactive with the particulate glass in a cement reaction, whereby the polymerizable polymer has a polymer backbone and pendant groups having one or more polymerizable carbon-carbon double bonds. Preferably, the pendant groups are hydrolysis stable. The aqueous dental glass ionomer composition may comprise one or more water-soluble, polymerizable polymers comprising acidic groups according to (B).

The water-soluble, polymerizable polymer according to (B) comprises acidic groups such as carboxylic acid groups at its backbone, and optionally, it may comprise further acidic groups at the pendant groups. The carboxylic acid groups of the polymer are capable of reacting with a reactive particulate glass in a cement reaction to form a glass ionomer cement.

The term "polymerizable polymer" used in connection with item (B) means a polymer containing one or more polymerizable moieties capable of polymerizing and cross-linking of the polymer for improving the mechanical properties and the long-term mechanical and chemical resistance of the cured aqueous dental glass ionomer composition.

The term "water-soluble" used in connection with the term "polymerizable polymer" means that at least 0.1 g, preferably 0.5 g of the polymerizable polymer dissolves in 100 g of water at 20° C.

The water-soluble polymerizable polymer according to (B) is preferably hydrolysis-stable, which means that the polymer is stable to hydrolysis in an acidic medium, such as in a dental composition. Specifically, the polymer preferably does not contain groups such as ester groups which hydrolyze in aqueous media at pH 3 at room temperature within one month.

Preferably, the water-soluble, polymerizable polymer comprising acidic groups according to (B) is obtained by a process comprising
  a) a step of copolymerizing a mixture comprising
    (i) a first copolymerizable monomer comprising at least one optionally protected carboxylic acid group and a first polymerizable organic moiety, and
    (ii) a second copolymerizable monomer comprising one or more optionally protected primary and/or secondary amino groups and a second polymerizable organic moiety, for obtaining an amino group containing copolymer;
  b) a step of coupling to the amino group containing copolymer a compound having a polymerizable moiety and a functional group reactive with an amino group of repeating units derived from the second copolymerizable monomer in the amino group containing copolymer obtained in the first step, wherein the optionally protected amino group is deprotected, so that polymerizable pendant groups are linked to the backbone by hydrolysis-stable linking groups,
  and, optionally, a step of deprotecting the protected carboxylic acid group after step a) or step b), for obtaining a polymerizable polymer.

The first copolymerizable monomer to be used in step a) comprises at least one, preferably one to three, more preferably one or two, most preferably one optionally protected carboxylic acid group(s).

The protecting group of an optionally protected carboxylic acid group is not particularly limited as long as it is a carboxyl-protecting group known to those of ordinary skill in the art of organic chemistry (cf. P. G. M. Wuts and T. W. Greene, Greene's Protective Groups in Organic Synthesis, 4th Edition, John Wiley and Sons Inc., 2007). Preferably, the carboxyl-protecting group is selected from a trialkylsilyl group, an alkyl group and an arylalkyl group. More preferably, the carboxyl-protecting group is selected from an alkyl group or an arylalkyl group. Most preferably, the carboxyl-protecting group is selected from a tert-butyl group and a benzyl group. In one preferred embodiment, the carboxyl-protecting group is a tert-butyl group.

The term "polymerizable organic moiety" as used herein means an organic moiety of a molecule which can be used to covalently link this molecule in a chemical reaction (polymerization) to other molecules reactive with this moiety to form a macromolecule of repeating or alternating structural units. Preferably, this polymerizable organic moiety is a carbon-carbon double bond as in the case of an ethylenically unsaturated moiety.

In a preferred embodiment of the aqueous dental glass ionomer composition of the present invention, the first copolymerizable monomer is represented by the general formula (1):

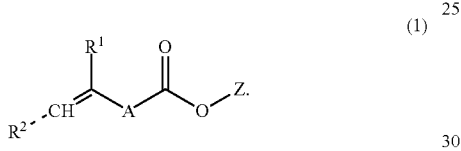

In formula (1), $R^1$ is a hydrogen atom, a —COOZ group or a straight chain or branched $C_{1-6}$ alkyl group which may be substituted by a —COOZ group. Preferably, $R^1$ is a hydrogen atom, a —COOZ group or a methyl group. More preferably, $R^1$ is a hydrogen atom or a methyl group.

In formula (1), $R^2$ is a hydrogen atom, a —COOZ group or a straight-chain or branched $C_{1-6}$ alkyl group which may be substituted by a —COOZ group. Preferably, $R^2$ is a hydrogen atom or a —COOZ group. More preferably, $R^2$ is a hydrogen atom. In formula (1), the dotted line indicates that $R^2$ may be in either the cis or trans orientation.

In formula (1), A is a single bond or a straight-chain or branched $C_{1-6}$ alkylene group which group may contain 1 to 3 heteroatoms in between two carbon atoms of the alkylene carbon chain, which heteroatoms are selected from an oxygen atom, nitrogen atom, and sulfur atom, and/or which alkylene group may contain in between two carbon atoms of the alkylene carbon chain 1 to 3 groups selected from an amide bond or a urethane bond. Preferably, A is a single bond or a straight-chain or branched $C_{1-6}$ alkylene group which group may contain a heteroatom in between two carbon atoms of the alkylene carbon chain, which heteroatom is selected from an oxygen atom or a nitrogen atom, and/or which alkylene group may contain in between two carbon atoms of the alkylene carbon chain a group selected from an amide bond or a urethane bond. More preferably, A is a single bond or a straight-chain $C_{1-6}$ alkylene group. Most preferably, A is a single bond.

In formula (1), Z which may be the same or different independently represents a hydrogen atom, a metal ion, a protecting group for a carboxylic acid group, or the Z forms with a further —COOZ group present in the molecule an intramolecular anhydride group. The metal ion may be a monovalent metal ion such as an alkali metal ion. In one embodiment, Z is a protecting group for a carboxylic acid group. In another embodiment, Z is a hydrogen atom. When Z forms with a further —COOZ group present in the molecule an intramolecular anhydride group (—C(O)OC(O)—), the further —COOZ group may be preferably present on $R^1$ such as in case of itaconic acid anhydride.

In a preferred embodiment, Z is a hydrogen atom and the polymerization reaction is conducted in an alkaline environment. In an alternative preferred embodiment, Z is a hydrogen atom and the amino groups of the first copolymerizable monomer and of the second copolymerizable monomer carry a protecting group.

Preferably, the first copolymerizable monomer is a protected (meth)acrylic acid monomer. More preferably, a first polymerizable monomer is selected from tert-butyl acrylate and benzyl acrylate. Most preferably, a first polymerizable monomer is tert-butyl acrylate.

In a preferred embodiment of the aqueous dental glass ionomer composition of the present invention, the second copolymerizable monomer is represented by the general formula (2):

In formula (2), $R^3$ is a hydrogen atom or a straight chain or branched $C_{1-6}$ alkyl group which may be substituted by a —COOZ' group. Preferably, $R^3$ is a hydrogen atom. In formula (2), the dotted line indicates that $R^3$ may be in either the cis or trans orientation.

In formula (2), X is a protected amino group or a hydrocarbon group having 1 to 20 carbon atoms, which is substituted with an amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. Preferably, X is a hydrocarbon group having 1 to 20 carbon atoms, which is substituted with an amino group which may carry a protecting group, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. More preferably, X is a hydrocarbon group having 1 to 20 carbon atoms, even more preferably 1 to 6 carbon atoms, which is substituted with an amino group which may carry a protecting group, wherein the hydrocarbon group may contain an oxygen atom and/or which hydrocarbon group may contain an amide bond and which hydrocarbon group may further be substituted with a —COOZ' group. In as specific embodiment wherein X is a protected amino group, the compound of formula (2) is ally amine, wherein the amino group carries a protecting group.

The protecting group of a protected amino group or an optionally protected amino group is not particularly limited and may be any conventional protecting group for an amino group as, for example, described in P. G. M. Wuts and T. W. Greene, Greene's Protective Groups in Organic Synthesis, 4th Edition, John Wiley and Sons Inc., 2007. Preferably, the amino-protecting group is selected from an acyl group, an arylalkyl group, an alkoxy carbonyl group, and an aryloxy-carbonyl group. More preferably, the amino-protecting group is an acyl group. Most preferably, the amino-protecting group is a formyl group.

In formula (2), Y is a hydrogen atom or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. Preferably, Y is a hydrogen atom or a hydrocarbon group having 1 to 20 carbon atoms, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. More preferably, Y is a hydrogen atom or a hydrocarbon group having 1 to 20 carbon atoms, even more preferably 1 to 6 carbon atoms, wherein the hydrocarbon group may contain an oxygen atom and/or which hydrocarbon group may contain an amide bond and which hydrocarbon group may further be substituted with a —COOZ' group. In one preferred embodiment, Y is a hydrogen atom.

In formula (2), Z which may be the same or different, independently represents a hydrogen atom, a metal ion, a protecting group for a carboxylic acid group, or the Z' forms with a further —COOZ' group present in the molecule an intramolecular anhydride group. In one embodiment, Z' is a protecting group for a carboxylic acid group. In another embodiment, Z' is a hydrogen atom. The metal ion may be a monovalent metal ion such as an alkali metal ion. In another embodiment, Z' is a hydrogen atom. When Z forms with a further —COOZ' group present in the molecule an intramolecular anhydride group (—C(O)OC(O)—).

In a preferred embodiment. Z' is a hydrogen atom and the polymerization reaction is conducted in an alkaline environment. In an alternative preferred embodiment, Z' is a hydrogen atom and the amino groups of the second copolymerizable monomer carry a protecting group.

In one embodiment, the second copolymerizable monomer comprises a second copolymerizable organic moiety selected from the group of (meth)acrylamide moieties which may be substituted and substituted (meth)acrylic acid which may be protected. In another embodiment, the second copolymerizable monomer is selected from allyl amine, aminopropyl vinyl ether, aminoethyl vinyl ether, N-vinyl formamide and 2-aminomethyl acrylic acid. In a preferred embodiment, the second copolymerizable monomer is aminopropyl vinyl ether. The amino group may be in the form of an ammonium salt such as a ammonium chloride. Preferred structures wherein the amino group may also carry a protecting group are depicted in Scheme 1 below.

Scheme 1

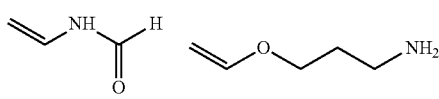

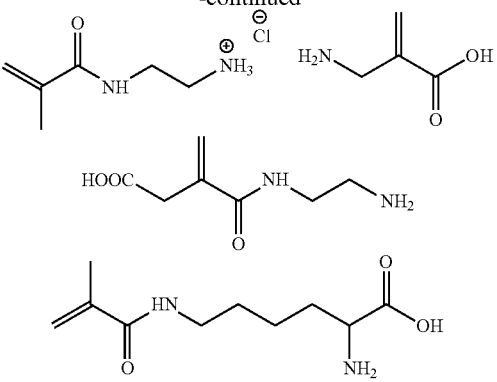

The molar ratio of first copolymerizable monomer to second copolymerizable monomer in the mixture copolymerized in step a) (mol first copolymerizable monomer/mol second copolymerizable monomer) is preferably in the range of from 100:1 to 100:50, more preferably in the range from 100:2 to 100:20, still more preferably in a range from 100:3 to 100:10.

The further copolymerizable monomers optionally to be used in step a) comprise at least one, preferably one to three, more preferably one or two, most preferably one optionally protected acidic group(s) which are not carboxylic acid groups. Specific examples of acidic groups are sulfonic acid groups (—SO$_3$M), phosphonic acid groups (—PO$_3$M$_2$) or phosphoric acid ester groups (—OPO$_3$M$_2$), or salts thereof, wherein M may independently be a hydrogen atom or a monovalent ion such as an alkali metal or an ammonium ion.

Specific examples of the optional further monomers are selected from 2-acrylamido-2-methylpropane sulfonic acid, vinyl phosphonate, and vinyl sulfonic acid.

In a preferred embodiment, the solutions containing the first copolymerizable monomer and the second copolymerizable monomer are separately saturated with nitrogen before combining them for copolymerization to minimize possible side-products of a competitive Aza-Michael addition.

Step a) for obtaining an amino group containing copolymer proceeds as a chain-growth polymerization. In one embodiment, step a) comprises radical copolymerization.

The type of copolymer formed by step a) of the present invention may be a statistical copolymer, a random copolymer, an alternating copolymer, a block copolymer or a combination thereof.

A copolymer obtained by step a) of the present invention is an amino group containing copolymer, such as, for example, a copolymer obtainable by copolymerization of acrylate and aminopropyl vinyl ether.

The reaction conditions of the polymerization reaction according to step a) of the present invention are not particularly limited. Accordingly, it is possible to carry out the reaction in the presence or absence of a solvent. A suitable solvent may be selected from the group of water, dimethyl formamide (DMF), tetrahydrofurane (THF), and dioxane.

The reaction temperature is not particularly limited. Preferably, the reaction is carried out at a temperature of between −10° C. to the boiling point of the solvent. Preferably, the reaction temperature is in the range of from 0° C. to 80° C.

The reaction time is not particularly limited. Preferably the reaction time is in the range of from 10 minutes to 48 hours, more preferably 1 hour to 36 hours.

The reaction is preferably carried out in the presence of a polymerization initiator. In a preferred embodiment of the aqueous dental glass ionomer composition, the polymerization initiator is selected from azobisisobutyronitrile (AIBN), 2,2-azobis(2-amidinopropane)dihydrochloride, 2,2'-azobis (2-methybutyronitrile), 2,2'-azobis(N,N'-dimethyleneisobutyramidine) dihydrochloride, and 4,4'-azobis(4-cyano pentanoic acid). The amount of the polymerization initiator is not particularly limited. Suitably, the amount is in the range of from 0.001 to 5 mol % based on the total amount of the monomers.

The reaction product obtained in step a) may be isolated by precipitation and filtration, or lyophilization. The product may be purified according to conventional methods.

Step b) for obtaining the water-soluble, polymerizable polymer comprising acidic groups according to (B) is a step of coupling a compound having a polymerizable moiety and a functional group reactive with an amino group of repeating units derived from the second copolymerizable monomer in the amino group containing copolymer obtained in step a) wherein the optionally protected amino group is deprotected.

Preferably, the coupling reaction in step b) is an addition reaction or a condensation reaction forming a bond selected from an amide bond, a urea bond or a thiourea bond.

The term "functional group reactive with an amino group" as used herein means any group which can form a covalent bond with an amino group of the amino group containing copolymer. Preferably, a functional group reactive with an amino group is a carboxylic acid group or a derivative thereof such as an ester group or an anhydride thereof, an isocyanate group or an isothiocyanate group. More preferably, a functional group reactive with an amino group is a carboxylic acid group or a derivative thereof.

If the amino group of repeating units derived from the second copolymerizable monomer in the amino group containing copolymer obtained in the first step is protected, the amino group can be deprotected prior to step b) or concomitant with step b).

The conditions for deprotection of an optionally protected amino group are selected according to the protecting group used. Preferably, the protected amino group is deprotected by hydrogenolysis or treatment with acid or base.

If the deprotection of a protected amino group is carried out concomitantly with step b), it will be understood by a person skilled in the art that the deprotection conditions and the conditions for step b) have to be selected so that both reactions can proceed efficiently.

In a preferred embodiment of the aqueous dental glass ionomer composition, the compound having a polymerizable moiety and a functional group reactive with an amino group of repeating units derived from the second copolymerizable monomer is a compound represented by the general formula (3):

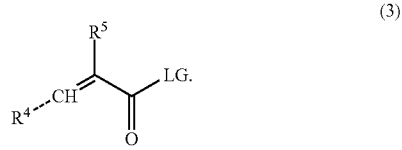

(3)

In formula (3), $R^4$ is a hydrogen atom or a straight chain or branched $C_{1-6}$ alkyl group which may be substituted by a —COOZ" group, and $R^5$ is a hydrogen atom or a straight-chain or branched $C_{1-6}$ alkyl group which may be substituted by a —COOZ" group. Preferably, $R^4$ is a hydrogen atom, and $R^5$ is a hydrogen atom or a methyl group. More preferably, $R^4$ is a hydrogen atom, and $R^5$ is a methyl group. In formula (3), the dotted line indicates that $R^4$ may be in either the cis or trans orientation.

In formula (3), Z" which may be same or different, independently represents a hydrogen atom, a metal ion, a protecting group for a carboxylic acid group, or the Z" forms with a further —COOZ" group present in the molecule an intramolecular anhydride group.

In one embodiment, Z" is a protecting group for a carboxylic acid group. In another embodiment, Z" is a hydrogen atom. In a preferred embodiment, Z" is a hydrogen atom and the polymerization reaction is conducted in an alkaline environment. In an alternative preferred embodiment, Z"s a hydrogen atom and the amino groups of the second copolymerizable monomer carry a protecting group.

In one embodiment, in formula (3), LG is a leaving group. Preferably, LG is a chlorine atom or a bromine atom, or forms with the adjacent carbonyl group a carboxylic acid anhydride moiety. More preferably, LG is a group which is suitable for reacting the compound of formula (3) in a Schotten-Baumann type reaction.

In another embodiment, LG may replace Z" and form with $R^4$ or $R^5$ an intramolecular carboxylic acid anhydride group.

In yet another embodiment two molecules of formula (3) form an intermolecular carboxylic acid anhydride group by sharing a common LG, wherein LG is an oxygen atom.

It is particularly preferred that the compound of formula (3) is acrylic acid, (meth)acrylic acid, crotonic acid, isocrotonic acid, tiglic acid, angelic acid, or an anhydride of the aforementioned acids formed of two identical or different acids; more preferably an anhydride of the aforementioned acids formed of two identical acids. Most preferably, the compound of formula (3) is (meth)acrylic anhydride.

The coupling according to step b) of the present invention serves to introduce one or more polymerizable moieties into the amino group containing copolymer, which moieties can be post-polymerized to provide additional covalent and advantageously also ionic crosslinking, imparting additional strength to the dental material.

In one embodiment of the aqueous dental glass ionomer composition, the carboxylic acid groups of the copolymer obtained in step b) are not protected and the copolymer can be used as a polymer according to the present invention without further treatment. In an alternative embodiment, the carboxylic acid groups of the copolymer obtained in step b) are protected and the carboxylic acid groups have to be deprotected before the copolymer exhibits the features of a polymer according to the present invention.

The reaction conditions of the reaction according to step b) of the present invention are not particularly limited. Accordingly, it is possible to carry out the reaction in the presence or absence of a solvent. A suitable solvent may be selected from the group of dimethyl formamide (DMF), tetrahydrofurane (THF), and dioxane.

The reaction temperature is not particularly limited. Preferably, the reaction is carried out at a temperature of between −10° C. to the boiling point of the solvent. Preferably, the reaction temperature is in the range of from 0° C. to 80° C.

The reaction time is not particularly limited. Preferably the reaction time is in the range of from 10 minutes to 48 hours, more preferably 1 hour to 36 hours.

The reaction product obtained in step b) may be isolated by precipitation and filtration. The product may be purified.

The aqueous dental glass ionomer composition optionally includes a step of deprotecting the protected carboxylic acid group after step a) or step b), for obtaining a polymerizable polymer. In a preferred embodiment, the aqueous dental glass ionomer composition includes a step of deprotecting the protected carboxylic acid group for obtaining a polymerizable polymer. In a further preferred embodiment, the aqueous dental glass ionomer composition includes a step of deprotecting the protected carboxylic acid group after step b).

The conditions for deprotection of an optionally protected carboxyl group are selected according to the protecting group used. Preferably, the protected carboxyl group is deprotected by hydrogenolysis or treatment with acid or base.

A first embodiment of the polymerizable polymer according to (B) is illustrated by the following Scheme 2, wherein a amino group protected vinyl amine is reacted with acrylic acid for obtaining a polymer backbone having a protected amino group. The copolymer is preferably a random copolymer. In a further step, the protected amino groups of the polymer backbone are liberated and coupled to a polymerizable group containing moiety, whereby a polymer of the invention is obtained having acidic groups reactive in a cement reaction wherein ionic bonds are formed, and having polymerizable groups reactive in a crosslinking reaction wherein covalent bonds are formed.

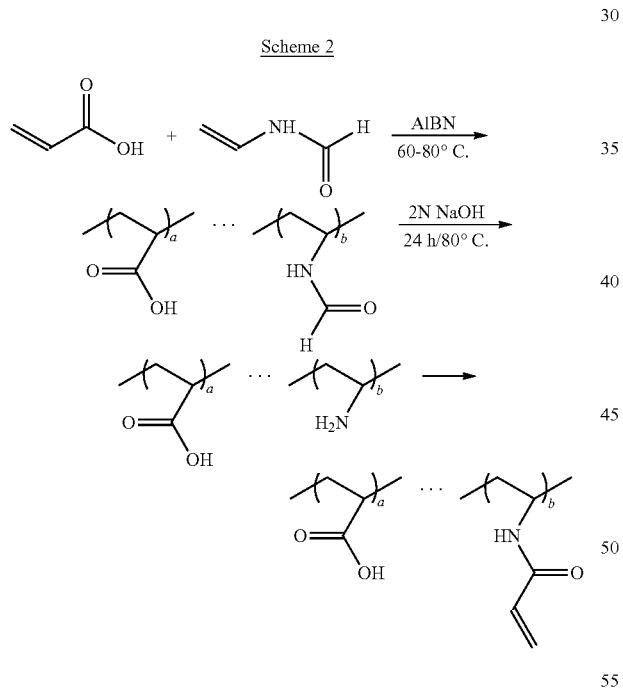

In above Scheme 2, any acrylamide group may be replaced by a methacrylamide group.

A second embodiment of the polymerizable polymer according to (B) is illustrated by the following Scheme 3, wherein protected acrylic acid is reacted with an amino group containing polymerizable vinyl ether derivative for obtaining an amino group containing polymer backbone. In a further step, the amino groups of the polymer backbone are couples to a polymerizable group containing moiety. Finally, the carboxylic acid groups are liberated whereby a polymer of the invention is obtained having acidic groups reactive in a cement reaction wherein ionic bonds are formed, and having polymerizable groups reactive in a crosslinking reaction wherein covalent bonds are formed.

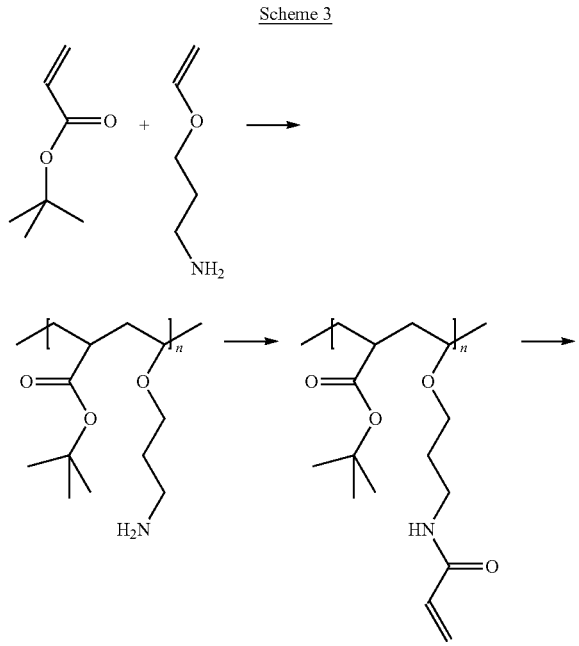

In the above Scheme 3, any acrylamide group may be replaced by a methacrylamide group The polymerizable polymer obtained in step b) may be exemplified by the following preferred structures depicted in Scheme 4 below.

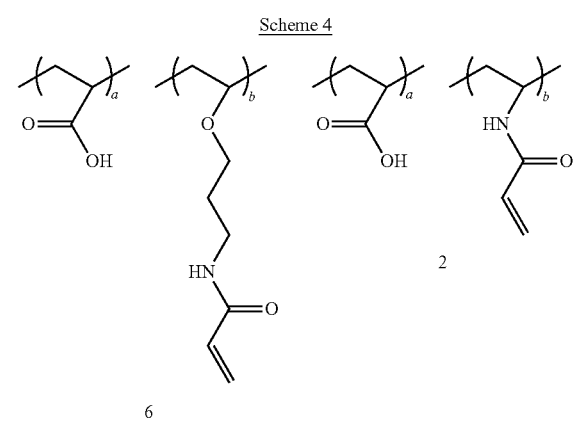

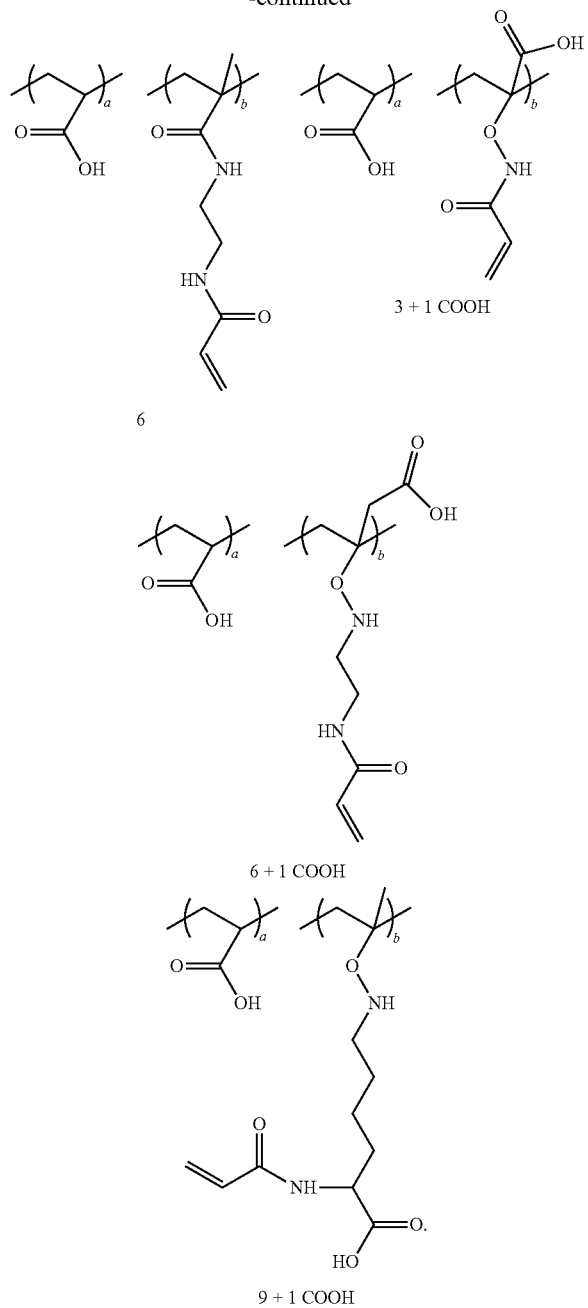

In the structures illustrated in Scheme 4, the numbers refer to the number of additional carbon atoms introduced by each of the side chain as compared to a corresponding polyacrylic acid. Since a polymer having (a+b) repeating units contains b times the number of additional carbon atoms in addition to the number of carbon atoms in a polyacrylic acid having (a+b) carboxylic acid groups, but b times less carboxylic acid groups, the water solubility may be reduced. On the other hand, the introduction of an additional ionic group such as a —COOH group is capable of compensating the decrease in water solubility, and is also indicated above. Preferably, the number of side chains b, the number of additional carbon atoms and the number of additional carboxylic acid groups are adjusted so as to provide a useful water solubility of the polymer of the present invention.

Accordingly, in a preferred embodiment, the side chains of the polymer which are linked to the polymer backbone via an amide bond, urea bond or thio urea bond contain one or more additional acidic groups, preferably carboxylic acid groups.

The polymerizable polymer according to (B) preferably has an average molecular weight $M_w$ in the range of from $10^3$, in particular $10^4$, to $10^6$ Da. More preferably, the average molecular weight $M_w$ is in the range of from $10^5$ to $7 \cdot 10^5$ Da, or $3 \cdot 10^4$ to $2.5 \cdot 10^5$ Da.

The polymerizable polymers according to (B) must be sufficient in number or percent by weight of carboxylic acid groups to bring about the setting or curing reaction in the presence of the reactive particulate glass according to (A) or any further unmodified or modified particulate reactive(s) and/or non-reactive filler(s). Preferably, the polymerizable polymer according to (B) is present in the aqueous dental glass ionomer composition in an amount of from 5 to 80 percent by weight, more preferably 10 to 50 percent by weight, still more preferably 15 to 40 percent by weight, based on the total weight of the composition.

(C The Polymerization Initiator System

As polymerization initiator system according to (C), any compound or system, capable of initiating the polymerization reaction according to the present invention may be suitably used. The polymerization initiator according to (C) may be a photoinitiator or a redox initiator or a mixture thereof.

The term "photoinitiator" means any chemical compound that forms free radicals when activated, e. g. by exposure to light or interaction with a coinitiator in a photochemical process.

The term "redox initiator" means a combination of an oxidizing agent and a reducing agent, and optionally a catalyst such as a metal salt. The redox initiator system provides a redox reaction in which radicals are formed. These radicals initiate polymerisation of a radically polymerizable compound. Typically, a redox initiator system is activated by bringing the redox initiator system in contact with water and/or an organic solvent providing for at least partial dissolution of the oxidising agent and the reducing agent. The optional catalyst may be added to accelerate the redox reaction and thus the polymerization of the radically polymerizable compound.

A mixture of a photoinitiator and a redox initiator is a "dual cure initiator system".

For example, a suitable photoinitiator system may be in the form of a binary or tertiary system. A binary system may include a photoinitiator and an electron donor compound. A tertiary system may include an iodonium, sulfonium or phosphonium salt, a photoinitiator, and an electron donor compound, as for example described in U.S. Pat. No. 5,545,676.

Suitable photoinitiators for the polymerization initiator system according to (C) are Norrish type I and Norrish type II photoinitiators.

Suitable Norrish type I photoinitiators are for example phosphine oxides.

Phosphine oxide photoinitiators may have a functional wavelength range of about 380 nm to about 450 nm, which include acyl and bisacyl phosphine oxides such as those described in U.S. Pat. No. 4,298,738. U.S. Pat. Nos. 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4- dimethylbenzoyl)phosphine oxide, tris(2-methoxybenzoyl) phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Suitable Norrish type II photoinitiators are for example monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphor quinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate or dimethylamino benzonitrile.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyidiethanolamine, N-lauryldiethanolamine, triethanolamine, 2-(dimethylamino) ethyl methacrylate, N-methyidiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

The photoinitiator system may further comprise diaryl iodonium salts, triaryl sulfonium salts and tetraaryl or tetraalkyl phosphonium salts. These salts may serve as a coinitiator for improving the polymerization performance of the photoinitiator, but they may also serve as an initiator for cationic polymerization.

For example, diaryl iodonium salt may be selected from the group consisting of (4-methylphenyl[4-(2-methytpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl) iodonium hexafluorophosphate, di(4-chlorophenyl)iodonium hexafluorophosphate, di(naphthyl)iodonium tetrafluoroborate, di(4-trifluoromethylphenyi)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-isopropyl-4'-methyldiphenyliodonium borate.

According to a particularly preferred embodiment, the iodonium compound is DPI hexafluorophosphate and/or 4-isopropyl-4'-methyldiphenyliodonium tetrakis(pentafluorophenyl) borate.

A preferred triaryl sulfonium salt is S-(phenyl)thianthrenium hexafluorophosphate of the following formula:

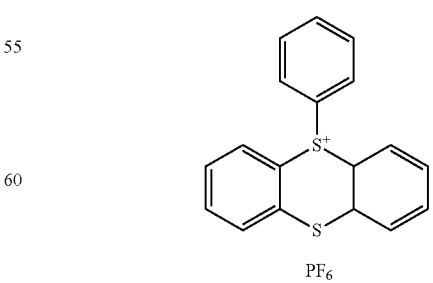

Particularly preferred phosphonium salts are the tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

A suitable redox initiator system comprises reducing and oxidizing agents, which produce free-radicals capable of initiating polymerization of the polymerizable group(s) of (B) the water-soluble, polymerizable polymer comprising acidic groups and optionally (D) the hydrolysis-stable, water-soluble monomer having a polymerizable double bond and optionally a carboxylic acid group and optionally of (E) the polymerizable hydrolysis-stable crosslinker having at least two polymerizable carbon-carbon double bonds, independent from the presence of light. The reducing and oxidizing agents are selected such that (C) the polymerization initiator system is sufficiently storage-stable and free of undesirable colorization to permit storage and use under typical dental conditions. Moreover, the reducing and oxidizing agents are selected so that (C) the polymerization initiator system is sufficiently miscible with the resin system to permit dissolution of the redox initiator system in the composition.

Useful reducing agents include ascorbic acid, ascorbic acid derivatives, and metal complexed ascorbic acid compounds as described in U.S. Pat. No. 5,501,727; amines, namely tertiary amines, preferably tertiary aromatic amines such as 4-tert-butyl dimethylaniline; aromatic sulfinate salts such as p-toluenesulfinate salts and benzenesulfinate salts, most preferably sodium para-toluenesulfinate; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof. Moreover, aliphatic sulfinate salts such as sulfinate salts having a straight chain or branched $C_{1-6}$ alkyl group are also preferred. Examples of aliphatic sulfonate salts include zinc isopropylsulfinate and zinc n-propylsulfinate, preferably zinc isopropylsulfinate.

Suitable oxidizing agents include persulfuric acid and salts thereof, such as ammonium, sodium, potassium, cesium, and alkyl ammonium salts, preferably inorganic peroxodisulfate salts, most preferably potassium peroxodisulphate. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

A particularly preferred redox initiator contains (i) an inorganic peroxodisulphate salt, (ii) an aromatic amine, and (iii) an aromatic or aliphatic sulfinate salt. For the particularly preferred redox initiator, it is preferred that the inorganic peroxodisulphate salt is potassium peroxodisulphate; and/or the aromatic amine is tert.-butyl-N,N-dimethylaniline (4-tert.-butyl-N,N-dimethylaniline); and/or the aromatic sulfinate salt is sodium para-toluenesulfinate and/or the aliphatic sulfonate salt is zinc isopropylsulfinate. Most preferably, the redox initiator contains (i') potassium peroxodisulphate, (ii') 4-tert.-butyl-N,N-dimethylaniline, and (iii') sodium para-toluenesulfinate and/or zinc isopropylsulfinate.

It is preferred that (C) the polymerization initiator system is a dual cure initiator system containing a photoinitiator and any one of the above described redox initiator systems. More preferably, the dual cure initiator system contains a photoinitiator (preferably α-diketone photoinitiator, more preferably camphor quinone) and the redox initiator contains (i) an inorganic peroxodisulphate salt, (ii) an aromatic amine, and (iii) an aromatic sulfinate salt and/or zinc aliphatic sulfonate salt. Most preferably, the dual cure initiator system contains a photoinitiator (preferably α-diketone photoinitiator, more preferably camphor quinone) and the redox initiator contains (i') potassium peroxodisulphate, (ii') tert.-butyl-N,N-dimethylaniline, and (iii') sodium para-toluenesulfinate and/or zinc isopropylsulfinate.

It was surprisingly found that when the present aqueous dental glass ionomer composition is self-cured, that is cured without applying an external power source such as a light source, the mechanical properties flexural strength and E-Modulus of the resulting self-cured composition can be significantly increased by the redox initiator containing (i) an inorganic peroxodisulphate salt, (ii) an aromatic amine, and (iii) an aromatic sulfinate salt.

For deep cavities, dark-curing polymerization initiator system according to (C) comprising a redox initiator are preferred. More preferred is a dual cure initiator system containing a photoinitiator and a redox initiator. The redox initiator is most preferably a redox initiator containing (i) an inorganic peroxodisulphate salt, (ii) an aromatic amine, and (iii) an aromatic sulfinate salt.

The amount of active species of the initiator system is not particularly limited. Suitably, the amount of photoinitiator in the polymerization initiator system (C) is in the range of from 0.001 to 5 mol % based on the total amount of the polymerizable compounds in the form of (B) the water-soluble, polymerizable polymer comprising acidic groups, the optional (D) hydrolysis-stable, water-soluble monomer having a polymerizable double bond and optionally a carboxylic acid group, and the optional (E) polymerizable hydrolysis-stable crosslinker having at least two polymerizable carbon-carbon double bonds.

(D) A Monomer Having a Single Polymerizable Double Bond

Optionally, the aqueous dental glass ionomer according to the invention comprises (D) a hydrolysis-stable, water-soluble monomer having a single polymerizable double bond. The aqueous dental glass ionomer according to the invention may comprise one or a mixture of two or more (D) hydrolysis-stable, water-soluble monomer having a single polymerizable double bond.

The term "hydrolysis-stable" used in this connection means that the monomer according to (D) is stable to hydrolysis in an acidic medium, such as in a dental composition. In particular, the monomer according to (D) does not contain groups, e.g. as ester groups, which hydrolyze in aqueous media at pH 3 at room temperature within one month.

Further, the term "water-soluble" used in this connection means that at least 0.1 g, preferably 0.5 g of the monomer according to (D) dissolves in 100 g of water at 20° C.

The optional hydrolysis-stable, water-soluble monomer according to (D) may provide for a further improvement of the mechanical characteristics of the present aqueous dental glass ionomer composition in cured form, since the monomer according to (D) polymerizes together with the polymerizable polymer according to (B) in the presence of the polymerization initiator system according to (C). Thereby, the monomer according to (D) may polymerize with itself and/or with the polymerizable pendant groups of the polymerizable compound according to (B). Hence, besides of the formation of a polymer formed of the monomer according to (D), a graft polymerization takes place wherein monomer(s) according to (D) react with the polymerizable pendant groups of the polymerizable polymer according to (B), whereby a graft polymer is formed. Furthermore, the graft side chains formed of the monomer according to (D) may additionally react with the pendant polymerizable groups of another polymerizable polymer according to (B), whereby a crosslinked polymer may be obtained.

In the following Scheme 5, graft polymerisation by means of the monomer according to (D) is exemplary depicted for the polymerizable polymer according to (B) illustrated in Scheme 3 above, wherein acrylic acid is merely exemplary selected as a monomer according to (D). The letter "m" denotes an integer of at least 1.

Scheme 5

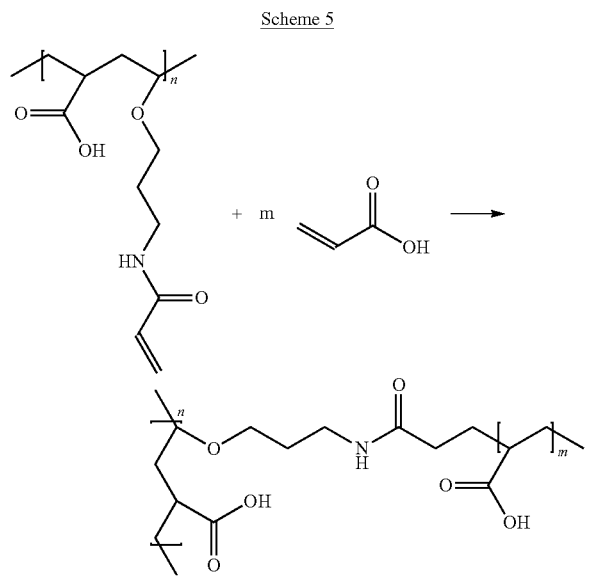

A suitable monomer according to (D) is hydrolysis stable, that is it does not contain groups hydrolysing at pH 3 within one month. In particular, a suitable monomer according to (D) does not contain any ester group.

Furthermore, a suitable monomer according to (D) contains one polymerizable double bond. Suitable polymerizable double bonds are carbon-carbon double bonds such as alkenyl groups and vinyl groups.

Preferably, the monomer according to (D) has a molecular weight of at most 200 Da, more preferably at most 150 Da, most preferably at most 100 Da.

Preferably, the hydrolysis-stable, water-soluble monomer having a single polymerizable double bond has a carboxylic acid group and is a compound represented by the general formula (4):

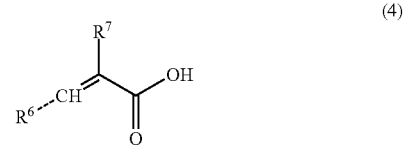

In formula (4), $R^6$ is a hydrogen atom or a straight chain or branched $C_{1-3}$ alkyl group, and $R^7$ is a hydrogen atom or a straight-chain or branched $C_{1-6}$ alkyl group which may be substituted by a —COOH group. In formula (4), the dotted line indicates that $R^6$ may be in either the cis or trans orientation. Preferably, $R^6$ is a hydrogen atom, and $R^7$ is a hydrogen atom or a $C_{1-3}$ alkyl group optionally substituted with a —COOH group. More preferably, $R^e$ is a hydrogen atom, and $R^7$ is a hydrogen atom or a methyl group substituted with a —COOH group, that is compound of formula (4) is acrylic acid or itaconic acid. Most preferably, the compound of formula (4) is acrylic acid.

It is preferred that in formula (4), residues $R^6$ and $R^7$ are selected with the proviso that the molecular weight of the monomer having a single polymerizable double bond according to (D) is at most 200 Da, preferably at most 150 Da, more preferably at most 100 Da.

Furthermore, the hydrolysis-stable, water-soluble monomer having a single polymerizable double bond may be 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide.

The monomer according to (D) is preferably selected in view of a good processability and applicability of the final aqueous dental glass ionomer composition, in particular in terms of viscosity. Therefore, the viscosity of the monomer according to (D) is preferably in the range of 0.1 to 100 mPa·s, more preferably 0.3 to 50 mPa·s, even more preferably 0.5 to 25 mPa·s, yet even more preferably 0.8 to 10 mPa·s, in particular 0.9 to 3 mPa·s.

Monomers according to (D) comprising a carboxylic acid group are particularly advantageous, since such monomers introduce additional carboxylic acid groups into the acidic polymer in the aqueous dental glass ionomer composition, which can undergo a cement reaction resulting in a further improved setting or curing reaction in the presence of the reactive particulate glass according to (A).

Preferably, the monomer according to (D) is contained in the aqueous dental glass ionomer composition in an amount of from 0.1 to 20, more preferably 1 to 15 even more preferably 2 to 10 percent by weight based on the total weight of the aqueous dental glass ionomer composition. When the monomer according to (D) is absent, a long-term mechanical resistance may be low. On the other hand, when the amount monomer according to (D) exceeds 20 percent of weight, shrinkage of the dental glass ionomer cement obtained from the present aqueous dental glass ionomer composition may occur.

(E) The Polymerizable Crosslinker Having at Least Two Polymerizable C—C Double Bonds Optionally, the aqueous dental glass ionomer composition according to the present invention contains (E) a polymerizable hydrolysis-stable crosslinker having at least two polymerizable carbon-carbon double bonds.

The crosslinker according to (E) may be an alkylenediol dimethylacrylate such as 1,3-butanediol dimethacrylate, 1,4-butanediol dimethacrylate, an alkylenediol divinyl ether such as 1,4-butanediol divinyl ether, di(ethylene glycol) dimethacrylate, di(ethylene glycol) divinyl ether, pentaerythritol diacrylate monostearate, ethylene glycol dimethacrylate, trimethylolpropane trimethacrylate, pentaerythritol triacrylate or triallyl ether, pentaerythritol tetraacrylate and trimethylolpropane triacrylate. The crosslinker according to (E) may also be 1,3-Bis(acrylamido)-N,N'-diethylpropane, N,N-Di(cyclopropyl acrylamido) propane.

Preferably, the crosslinker is a polymerizable compound of the following formula (5), which is disclosed in EP2705827 and WO2014040729:

(5)

wherein
A" is a group of the following formula (6)

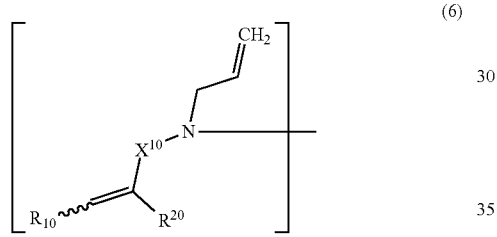

(6)

$X^{10}$ is CO, CS, $CH_2$, or a group $[X^{100}Z^{10}]_k$, wherein $X^{100}$ is an oxygen atom, a sulfur atom or NH, $Z^{10}$ is a straight chain or branched $C_{1-4}$ alkylene group, and k is an integer of from 1 to 10;

$R^{10}$ is a hydrogen atom, —$COOM^{10}$,
a straight chain or branched $C_{1-16}$ alkyl group which may be substituted by a $C_{3-6}$ cycloalkyl group, a $C_{6-14}$ aryl or $C_{34}$ heteroaryl group, —$COOM^{10}$, —$PO_3M^{10}$, —O—$PO_3M^{10}_2$ or —$SO_3M^{10}$,
a $C_{3-6}$ cycloalkyl group which may be substituted by a $C_{1-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$,
a $C_{6-14}$ aryl or $C_{3-14}$ heteroaryl group which may be substituted by —$COOM^{10}$, —$PO_3M^{10}$, —O—$PO_3M^{10}_2$ or —$SO_3M^{10}$, $R^{20}$ is a hydrogen atom,
—$COOM^{10}$
a straight chain or branched $C_{1-16}$ alkyl group which may be substituted by a $C_{6-14}$ aryl or $C_{3-14}$ heteroaryl group, —$COOM^{10}$, —$PO_3M^{10}$, —O—$PO_3M^{10}_2$ and —$SO_3M^{10}$,
a $C_{3-6}$ cycloalkyl group which may be substituted by a $C_{1-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$, or
a $C_{6-14}$ aryl or $C_{3-14}$ heteroaryl group which may be substituted by —$COOM^{10}$, —$PO_3M^{10}$, —O—$PO_3M^{10}_2$ and —$SO_3M^{10}$,
L is a single bond or a linker group;

B independently is
a group according to the definition of A",
a group of the following formula (7)

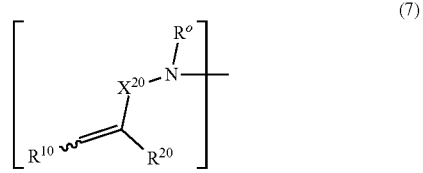

(7)

wherein
$X^{20}$ independently has the same meaning as defined for $X^1$ in formula (6),
$R^{10}$ and $R^{20}$ are independent from each other and independently have the same meaning as defined for formula (6),
$R°$ is a hydrogen atom.
a straight chain or branched $C_{1-16}$ alkyl group which may be substituted by a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$,
a $C_{3-6}$ cycloalkyl group which may be substituted by a $C_{1-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$,
a $C_{6-14}$ aryl group which may be substituted by —$COOM^{10}$, —$PO_3M^{10}$, —O—$PO_3$ $M^{10}_2$ or —$SO_3M^{10}$,
a group of the following formula (8)

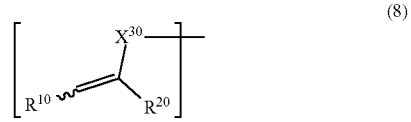

(8)

wherein
$X^{30}$ is CO, —$CH_2CO$—, CS, or —$CH_2CS$—,
$R^{10}$ and $R^{20}$ which are independent from each other and independently have the same meaning as defined for formula (6), or
a group $[X^{40}Z^{200}]_pE$,
wherein
$Z^{200}$ is a straight chain or branched $C_{1-4}$ alkylene group,
$X^{40}$ is an oxygen atom, a sulfur atom or NH,
E is a hydrogen atom,
$PO_3M_2$,
a straight chain or branched $C_{1-16}$ alkyl group which may be substituted by a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$,
a $C_{3-6}$ cycloalkyl group which may be substituted by a $C_{1-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$,
a $C_{6-14}$ aryl or $C_{3-14}$ heteroaryl group which may be substituted by —$COOM^{10}$, —$PO_3M^{10}$, —O—$PO_3M^{10}_2$ or —$SO_3M^{10}$, and
p is an integer of from 1 to 10;
and
n' is an integer of from 1 to 4;

wherein $M^{10}$ which are independent from each other each represent a hydrogen atom or a metal atom. Preferably, when L is a single bond, B cannot be a group according to the definition of A" or a group of the formula (7).

The following groups are preferred groups of formula (6), wherein M is a hydrogen atom or a metal atom:

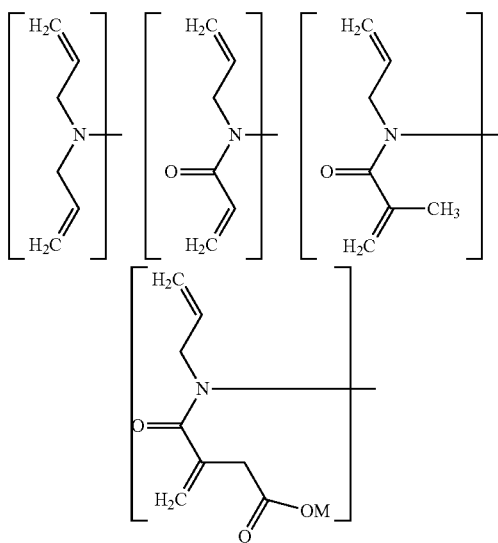

Preferred divalent linker groups may be selected from methylene, ethylene, propylene, butylene and the following divalent groups:

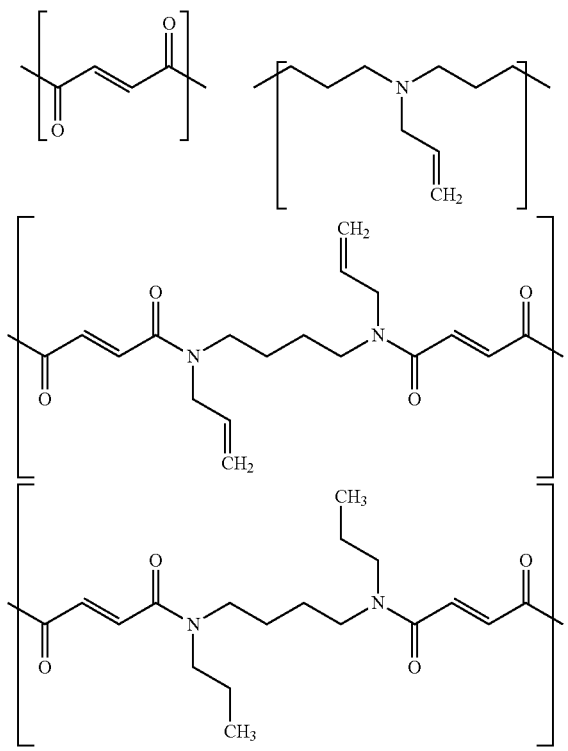

N,N'-(2E)-but-2-en-1,4-diallylbis-[(N-prop-2-en-1) amide and N,N-di(allyl acrylamido) propane are preferred.

Further Optional Components

The aqueous dental glass ionomer composition according to the present invention may, besides of optional components (D) and (E), comprise additional optional components.

For example, the aqueous dental glass ionomer composition according to the present invention may also include further components to improve the radio-opacity, such as $CaWO_4$, $ZrO_2$, $YF_3$ or to increase the fluoride release such as $YF_3$.

For example, the aqueous dental glass ionomer composition according to the present invention may also include a modifying agent such as tartaric acid. Such modifying agent provides for adjusting the working time and a setting time of the glass ionomer cement reaction, respectively, when preparing the cement as described in U.S. Pat. Nos. 4,089,830, 4,209,434, 4,317,681 and 4,374,936. In general, an increase in working time results in an increase in setting time as well.

The "working time" is the period of time that was measured from the start of mixing the powder and glass in the shown P/L ratio, during which it is possible to manipulate the material without an adverse effect on the properties.

The "setting time" is the point of time at which the mixture stopped being deformable, even under pressing.

In a setting reaction, due to the presence of polymerizable double bonds, a polymerization reaction takes place.

The aqueous dental glass ionomer composition according to the present invention may contain further components such as solvents, pigments, nonvitreous fillers, free radical scavengers, polymerization inhibitors, reactive and nonreactive diluents e.g. bisacrylamides such as N,N'-diethyl-1, 3-bisacrylamido-propan (BADEP), 1,3-bisacrylamido-propan (BAP), and 1,3-bisacrylamido-2-ethyl-propan (BAPEN), surfactants (such as to enhance solubility of an inhibitor e. g., polyoxyethylene), coupling agents to enhance reactivity of fillers e.g., 3-(trimethoxysilyl) propyl methacrylate, and rheology modifiers.

Suitable reactive diluents are alpha,beta unsaturated monomers for providing altered properties such as toughness, adhesion, and set time. Such alpha,beta-unsaturated monomers may be acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bisphenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2-bis(4-acryloxypropoxyphenyl)propane, 2,2-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2-bis[3(4-phenoxy)-2-hydroxypropane-1-acrylate]propane, may be mentioned. Other suitable examples of polymerizable components are isopropenyl oxazoline, vinyl azolactone, vinyl pyrrolidone, styrene, divinylbenzene, urethane acrylates or methacrylates, epoxy acrylates or methacrylates and polyol acrylates or methacrylates. Mixtures of alpha,beta-unsaturated monomers can be added if desired. Preferably, the mixed but unset dental compositions of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset aqueous dental glass ionomer composition components.

An example of a suitable free radical scavenger is 4-methoxyphenol.

It is preferred that the aqueous dental glass ionomer composition according to the present invention comprises an inhibitor of the following formula (9) and/or (10):

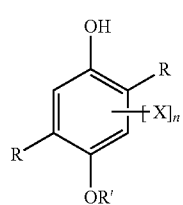
(9)

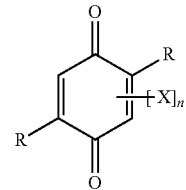
(10)

wherein
the Rs, which may be the same or different, independently represent a branched $C_{3-8}$ alkyl or alkenyl group, or a $C_{3-8}$ cycloalkyl or cycloakenyl group,
R' represents a hydrogen atom, a $C_{1-6}$ alkyl or $C_{2-6}$ alkenyl group, or a $C_{1-6}$ fluoroalkyl or $C_{2-6}$ fluoroalkenyl group,
X represents a group selected from a $C_{1-8}$ alkyl group or a $C_{3-8}$ cycloalkyl group, and
n is 0, 1 or 2.

The aqueous dental glass ionomer composition according to the present invention may comprise one or a mixture of two or more inhibitor(s) of the formula (9) and/or (10). Preferably, the inhibitor is a compound of formula (9) and/or (10) wherein Rs, which may be the same or different, independently represent a branched $C_{3-8}$ alkyl group or a $C_{3-8}$ cycloalkyl group, R' represents a hydrogen atom, a $C_{1-6}$ alkyl group or a $C_{1-6}$ fluoroalkyl group, and n is 0 or 1; more preferably, the inhibitor is a compound of formula (9) and/or (10) wherein Rs, which may be the same or different, independently represent a branched $C_{3-6}$ alkyl group, R' represents a hydrogen atom or a $C_{1-6}$ alkyl group, and n is 0; even more preferably, the inhibitor is a compound of the following formulae (9a), (9b) or (10a):

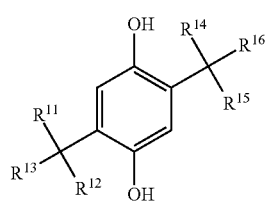
(9a)

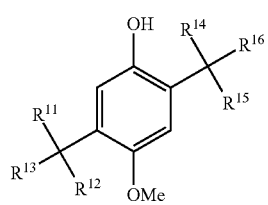
(9b)

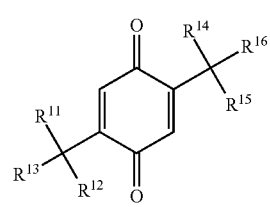
(10a)

wherein the $R^{11}$, $R^{12}$, $R^{13}$, $R^{14}$, $R^{15}$ and $R^{16}$, which may be the same or different, independently represent a methyl or an ethyl group. It is particularly preferred that the inhibitor of formulae (9a), (9b) or (10a) is a compound of the following formulae:

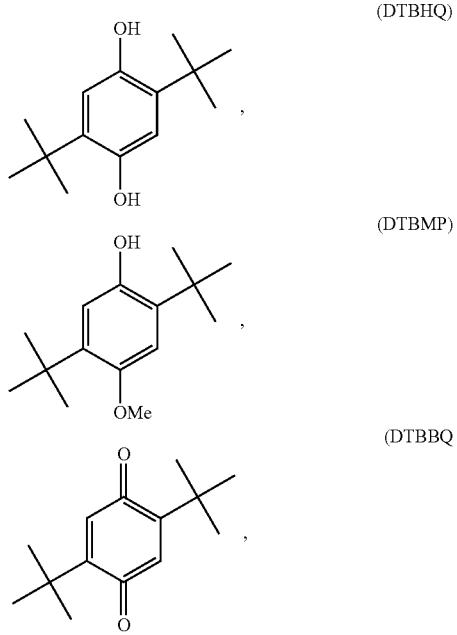

preferably DTBHQ.

2,5-di-tert-butyl-hydroquinone (DTBHQ), 2,5-di-tert-butyl-4-methoxyphenol and 2,5-di-tert-butyl-benzoquinone (DTBBQ) are commercially available standard chemicals. In general, monoethers of formula (9) with R' being $C_{1-6}$ alkyl, a $C_{2-6}$ alkenyl group, a $C_{1-6}$ fluoroalkyl or $C_{2-6}$ fluoroalkenyl group, such as 2,5-di-tert-butyl-hydroquinone monoalkylethers of formula (Ib), may be readily obtained from a dihydroquinone of formula (9), such as DTBHQ, as starting material by means of selective monoetherification catalyzed in the presence of $NaNO_2$ in combination with an inorganic acid such $H_2SO_4$ or a solid acidic catalyst such as a styrene based sulfonated polymer, e.g. the commercially available ion exchange resins Amberlyst® 15 and Aberlite® IR120, analogously as described by C. Gambarotti et al. in *Current Organic Chemistry* 2013, 17, pages 1108 to 1113. Alternatively, monoethers of formula (9) with R' being $C_{1-6}$ alkyl, a $C_{2-6}$ alkenyl group, a $C_{1-6}$ fluoroalkyl or $C_{2-6}$ fluoroalkenyl group, such as 2,5-di-tert-butyl-hydroquinone monoalkylethers of formula (Ib), may be obtained by reacting a dihydroquinone of formula (9), such as DTBHQ, with an alkyl alcohol in the presence of a transition metal salt selected from copper and iron salts analogously as described in the U.S. Pat. No. 4,469,897.

The inhibitor DTBHQ is particularly preferred, since from the present experimental Examples it appears that this inhibitor provides the best results in view of the discoloration problematic, i.e. there is no or almost no discoloration of the aqueous dental glass ionomer composition upon storage at 50° C. for 30 days.

According to an alternative embodiment, compounds of formula (9) are preferred in which R' represents a $C_{1-6}$ alkyl or $C_{2-6}$ alkenyl group, or a $C_{1-6}$ fluoroalkyl or $C_{2-6}$ fluoroalkenyl group. More preferably, R' represents a $C_{1-6}$ alkyl group or a $C_{1-6}$ fluoroalkyl group, and most preferably, R' represents a $C_{1-6}$ alkyl group.

The aqueous dental glass ionomer composition according to the invention contains the inhibitor in an amount of 0.001 to 3 percent by weight, preferably 0.005 to 2 percent by weight, more preferably 0.01 to 1.2 percent by weight and even more preferably 0.05 to 1.0 percent by weight, yet even more preferably 0.075 to 0.9 percent by weight, and most preferably 0.1 to 0.8 percent by weight based on the total weight of the liquid part of the aqueous dental composition.

When the amount of the Inhibitor is below the above indicated lower limit of 0.001, then storage stability of the aqueous dental glass ionomer composition might be insufficient, since the amount of inhibitor is too small to provide a stabilizing effect. However, when the amount of inhibitor is above the maximum threshold of 3 percent by weight, then the applicability of the aqueous dental glass ionomer composition might be negatively affected, since higher amounts of inhibitor may disturb or even substantially prevent intended polymerisation curing of the composition during application.

In order to provide an advantageous stability of the aqueous dental glass ionomer composition upon storage and/or during photo curing, to prevent or substantially prevent discoloration of said composition but also to provide a beneficial polymerization rate for photo curing, it may be preferred to set the molar ratio of (ii)(a) 1,2-diketone photoinitiator: (ii)(b) coinitiator compound:inhibitor(s) of formulae (9) and (10) within the range of 1:(0.3 to 3.0):(0.01 to 0.2), more preferably 1:(0.5 to 3.0):(0.01 to 0.1), even more preferably 1:(1.0 to 3.0):(0.01 to 0.05).

The aqueous dental glass ionomer composition according to the present invention may comprise further filler(s) besides of the reactive particulate glass according to (A). Preferably, the further filler(s) are selected from inert glass(es), fluoride releasing glass(es), granulated prepolymerized fillers, ground prepolymerized fillers and filler aggregates.

The term "inert glass(es)" refers to a glass which is not capable of reacting with a polymer containing acidic groups in a cement reaction. Inert glasses are for example described in the Journal of Dental Research June 1979, pages 1607-1619, or more recently in U.S. Pat. Nos. 4,814,362, 5,318,929, 5,360,770, and application US 200410079258 A1. Specifically, from US 2004/0079258 A1, inert glasses are known in which strongly basic oxides such as CaO, BaO, SrO, MgO, ZnO, $Na_2O$, $K_2O$, $Li_2O$ etc. are replaced with weakly basic oxides such as those in the Scandium or Lanthanide series.

The term "fluoride releasing glass(es)" refers to a glass capable of releasing fluoride. Fluoride releasing capability may be provided by adding to a mixture of oxides for forming a glass inorganic particles containing fluoride with the proviso that the glass has fluoride releasability, preferably sustained fluoride releasability. Such inorganic particles may be selected from the group consisting of sodium fluoride, strontium fluoride, lanthanum fluoride, ytterbium fluoride, yttrium fluoride, and calcium-containing fluoroaluminosilicate glasses.

The term "silanated" as used herein means that the filler has silane coupling agent(s) on its surface, for example in the form of a coating at least partly, and preferably fully covering the surface of the filler.

Typically, the silane coupling agent(s) are organosilanes of formula (11)

$$(R_{24}, R_{25}, R_{26})Si(R_H)_n \tag{11}$$

are applied, wherein n is 1 to 3 and the number of substituents $R_{24}$, $R_{25}$, $R_{26}$ is 4-n, wherein at least one of $R_{24}$, $R_{25}$, $R_{26}$ represents a polymerizable group. $R_H$, which may be the same or different if two or three groups $R_H$ are present, represent(s) a hydrolysable group capable of reacting with the surface of the filler material to be coated. $R_H$ may be selected from the group consisting of alkoxy groups, ester groups, halogen atoms and amino group, wherein the alkoxy groups are preferably linear $C_{1-8}$ or branched or cyclic $C_{3-8}$ alkoxy groups, and the ester groups are preferably carboxylates having linear $C_{1-8}$ or branched or cyclic $C_{3-8}$ alkyl groups. Most preferably, the hydrolysable group $R_H$ represents an alkoxy group.

The groups $R_{24}$, $R_{25}$ and $R_{26}$ may be the same or different and represent unreactive groups and/or polymerizable groups, with the proviso that at least one of $R_{24}$, $R_{25}$ and $R_{26}$ represents a polymerizable group. Unreactive groups for $R_{24}$, $R_{25}$ and $R_{26}$ may be represented by alkyl groups, preferably linear $C_{1-8}$ or branched or cyclic $C_{3-8}$ alkyl groups. Polymerizable groups for $R_{24}$, $R_{25}$ and $R_{26}$ are preferably selected from the group consisting of a (meth) acryl group, a vinyl group or an oxirane group, more preferably (meth)acryl group or a vinyl group, and most preferably a (meth)acryl group which may be in the form of e.g. methacryloxy or methacryloxyalkyl wherein alkyl means a linear $C_{1-8}$ or branched or cyclic $C_{3-8}$ alkyl group.

Particularly preferred organosilanes are for example 3-methacryloxy trimethoxysilane, vinyltrichlorosilane, tris (2-methoxyethoxy)-vinylsilane or tris(acetoxy)-vinylsilane, or any one of the specific group of organosilanes disclosed in EP 0 969 789 A1, namely 3-methacryl-oxypropyltrimethoxysilane, 3-methacryloxypropyldimethoxy-monochlorosilane, 3-methacryl-oxypropyldichloromonomethoxysilane, methacryloxypropyltri-chlorosilane, 3-methacryloxy-propyldichloromonomethyl-silane and 3-methacryloxypropylmonochlorodimethylsilane.

Alternatively, or additionally to the organosilanes of formula (11), so-called dipodal organosilanes may be applied. Dipodal organosilanes are typically compounds of formula (12)

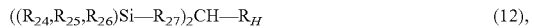

$$((R_{24},R_{25},R_{26})Si\!-\!R_{27})_2CH\!-\!R_H \quad (12),$$

wherein $R_{24}$, $R_{25}$, $R_{26}$ and $R_H$ have the same meaning as defined above for the organosilane of formula (11), and $R_{27}$ represents an alkylene group, preferably a linear $C_{1-8}$ or branched or cyclic $C_{3-8}$ alkylene group.

The aqueous dental glass ionomer composition according to the present invention preferably contains the further filler in an amount of 1 to 85 percent by weight based on the total weight of the composition.

Filler aggregates may be obtained by a process comprising:
a) coating a particulate filler, preferably a particulate glass filler as described above, which has a median particle size (D50) of from 1 to 1200 nm, with a coating composition containing a polymerizable film-forming agent forming a polymer coating layer on the surface of the particulate filler, said polymer coating layer may display reactive groups on the surface of the coating layer, said reactive groups being selected from addition polymerizable groups and step-growth polymerizable groups, thereby forming a coated particulate filler; subsequently or concurrently
b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;
c) optionally milling, classifying and/or sieving the granulation of the coated particulate filler; and
d) optionally further crosslinking the granulation of the coated particulate filler; for providing composite filler particles having a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles as further described in EP 2 604 247 A1.

For obtaining granulated and ground prepolymerized fillers, step b) of the above described process is omitted, and the milling step c) is applied with a suitable milling apparatus to attain an appropriate granulation particle size or ground particle size.

One-Pack or Multi-Pack Dental Composition

The present aqueous dental glass ionomer composition may be a one-pack or a multi-pack dental composition.

The term "one-pack" as used herein means that all components of the aqueous dental glass ionomer composition are comprised in one single pack such as a capsule having at least two chambers.

The term "multi-pack" as used herein means that the components of the aqueous dental glass ionomer composition are comprised in a multitude of separate packs. For example, a first part of components is comprised in a first pack, while as second part of components is comprised in a second pack, a third part of components may be comprised in a third pack, a fourth part of components may be comprised in a fourth pack, and so on.

Preferably, the aqueous dental glass ionomer composition is a composition of two or more packs, more preferably a two-pack composition. For a two-pack dental composition, a two-pack powder/liquid composition is preferred.

Preferably, in a two-pack powder/liquid composition, the liquid pack comprises water and (B) the water-soluble, polymerizable polymer comprising acidic groups, and the powder pack comprises (A) the reactive particulate glass.

More preferably, in the two-pack powder/liquid composition, the liquid pack comprises water, (B) the water-soluble, polymerizable polymer comprising acidic groups, (D) the hydrolysis-stable, water-soluble monomer having a single polymerizable double bond and optionally a carboxylic acid group a photoinitiator and optionally an inhibitor and optionally an aromatic amine (ii), and the powder pack comprises (A) the reactive particulate glass, optionally an inorganic peroxodisulphate salt (i) and optionally an aromatic sulfinate salt (iii). Most preferably, in the two-pack powder/liquid composition, the liquid pack comprises water, (B) the water-soluble, polymerizable polymer comprising acidic groups, (D) the hydrolysis-stable, water-soluble monomer having a single polymerizable double bond and optionally a carboxylic acid group, a photoinitiator, an inhibitor and an aromatic amine (ii), and the powder pack comprises (A) the reactive particulate glass, a solid inorganic peroxodisulphate salt (i) and an aromatic sulfinate salt (iii).

The Cured Aqueous Dental Glass Ionomer Composition

The present aqueous dental glass ionomer composition is a curable dental composition. That is a cured dental glass ionomer composition/cement can be obtained therefrom by polymerizing the polymerizable polymer according to (B)

and the monomer according to (C) in the presence of the reactive particulate glass (A) and the polymerization initiator system according to (D).

It was found that the present dental glass ionomer composition may have particularly advantageous mechanical properties:

Said composition's flexural strength is of at least 80 MPa as measured according to ISO 4049; and/or said composition's adhesion to enamel and/or dentine is of at least 5 MPa as measured according to ISO 29022:2013.

For the cured present dental glass ionomer composition, a high flexural strength of at least 80 MPa as measured according to ISO 4049 was obtained in all experimental examples when the composition was light-cured. Surprisingly, self-cured present dental glass ionomer compositions may also attain such high flexural strength, in particular in case the present dental glass ionomer composition comprises a polymerization initiator system in the form of a dual-cure initiator system containing a photoinitiator and a redox initiator, which redox initiator contains (i) an inorganic peroxodisulphate salt, (ii) an aromatic amine, and (iii) an aromatic sulfinate salt.

Particularly Preferred Embodiments of the Aqueous Dental Glass Ionomer Composition According to a particularly preferred embodiment, the aqueous dental glass ionomer composition according to the invention comprises (A) a reactive particulate glass comprising
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride, (B) a water-soluble, polymerizable polymer comprising acidic groups, which is reactive with the particulate glass in a cement reaction, whereby the polymerizable polymer has a polymer backbone and hydrolysis-stable pendant groups having a single or more polymerizable carbon-carbon double bonds, wherein the polymerizable polymer is obtainable by a process comprising
a) a step of copolymerizing a mixture comprising
(i) a first copolymerizable monomer is represented by the general formula (1'):

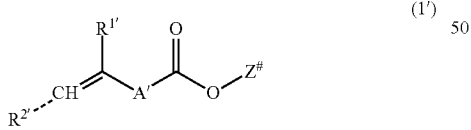

wherein
$R^{1'}$ is a hydrogen atom, a —$COOZ^{\#}$ group or a methyl group;
$R^{2'}$ is a hydrogen atom or a —$COOZ^{\#}$ group;
A' is a single bond or a straight-chain or branched $C_{1-6}$ alkylene group;
$Z^{\#}$ which may be the same or different, independently represents a hydrogen atom or a protecting group for a carboxylic acid group.
(ii) a second copolymerizable monomer represented by the general formula (2'):

wherein
$R^3$ is a hydrogen atom;
X' is a protected amino group or a hydrocarbon group having 1 to 6 carbon atoms, which is substituted with an amino group which may carry a protecting group, wherein the hydrocarbon group may contain a nitrogen atom;
Y' is a hydrogen atom or a hydrocarbon group having 1 to 6 carbon atoms, wherein the hydrocarbon group may contain an oxygen atom or an amide bond, and which hydrocarbon group may further be substituted with a —$COOZ^{\#\#}$ group;
$Z^{\#\#}$ which may be the same or different, independently represents a hydrogen atom or a protecting group for a carboxylic acid group, for obtaining an amino group containing copolymer;

b) a step of coupling to the amino group containing copolymer a compound having a polymerizable moiety and a functional group represented by the general formula (3'):

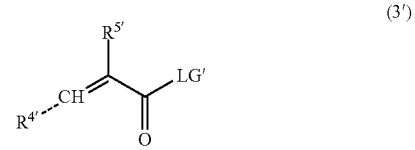

wherein
$R^{4'}$ is a hydrogen atom or a methyl group;
$R^{5'}$ is a hydrogen atom or a methyl group;
LG' is a chlorine atom or a bromine atom, or forms with the adjacent carbonyl group a carboxylic acid anhydride moiety, or wherein
two molecules of formula (3) form an intermolecular carboxylic acid anhydride group by condensation of LG', wherein LG' is an oxygen atom,
wherein the optionally protected amino group is deprotected, so that polymerizable pendant groups are linked to the backbone by hydrolysis-stable linking groups, and, optionally, a step of deprotecting the protected carboxylic acid group after step a) or step b), for obtaining a polymerizable polymer having an average molecular weight $M_w$ in the range of from $3 \cdot 10^4$ to $2.5 \cdot 10^5$ Da;

(C) a polymerization initiator system being based on a radical initiator in the form of a photoinitiator optionally in combination with a redox initiator, preferably a monoketone or diketone photoinitiator, more preferably an α-diketone photoinitiator, most preferably camphor quinone, optionally in combination with a redox initiator containing (i) an inorganic peroxodisulphate salt, preferably potassium peroxodisulphate;

(ii) an aromatic amine, preferably tert.-butyl-N,N-dimethylaniline, and
(iii) an aromatic sulfinate salt, preferably sodium para-toluenesulfinate;
most preferably in combination with a redox initiator containing
(i') potassium peroxodisulphate,
(ii') tert.-butyl-N,N-dimethylaniline, preferably 4-tert.-butyl-N,N-dimethylaniline, and
(iii') sodium para-toluenesulfinate;
(D) optionally a hydrolysis-stable, water-soluble monomer having a single polymerizable double bond and a carboxylic acid group, said monomer having a molecular weight of at most 200 Da; preferably said monomer is a compound represented by the general formula (4'):

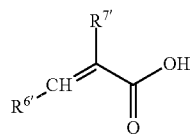

wherein
$R^{6'}$ is a hydrogen atom or a straight chain or branched $C_{1-3}$ alkyl group, and
$R^{7'}$ is a hydrogen atom or a straight-chain or branched $C_{1-3}$ alkyl group which may be substituted by a —COOH group, wherein $R^{6'}$ and $R^{7'}$ are selected with the proviso that the molecular weight of the compound of formula (4) is at most 200 Da;
preferably,
$R^{6'}$ is a hydrogen atom, and
$R^{7'}$ is a hydrogen atom or a $C_{1-3}$ group optionally substituted with a —COOH group;
more preferably,
$R^{6'}$ is a hydrogen atom, and
$R^{7'}$ is hydrogen atom or a methyl group substituted with a —COOH group.

In this particularly preferred embodiment, it is most preferred that (C) the polymerization initiator system is based on an α-diketone photoinitiator, preferably camphor quinone, in combination with a redox initiator containing
(i') potassium peroxodisulphate,
(ii') 4-tert.-butyl-N,N-dimethylaniline, and
(iii') sodium para-toluenesulfinate.

Furthermore, in this particularly preferred embodiment, it is preferred to select the first copolymerizable monomer represented by the general formula (1/1'), the second copolymerizable monomer represented by the general formula (2/2'), the compound having a polymerizable moiety and a functional group reactive with an amino group of repeating units derived from the second copolymerizable monomer represented by the general formula (3/3') and the hydrolysis-stable, water-soluble monomer having a single polymerizable double bond represented by the general formula (4/4') as follows:
the first copolymerizable monomer:
is a protected (meth)acrylic acid monomer, more preferably tert-butyl acrylate or benzyl acrylate, most preferably tert-butyl acrylate;
the second copolymerizable monomer:
is an aminopropyl vinyl ether wherein the amino group may be in the form of an ammonium salt such as ammonium chloride, more preferably a compound selected from the following, wherein the amino group may also carry a protecting group:

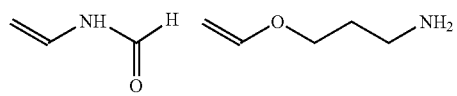

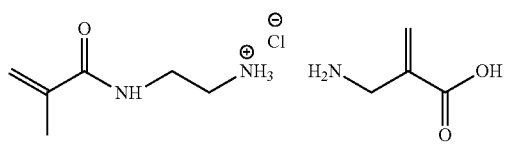

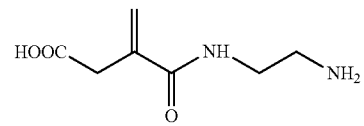

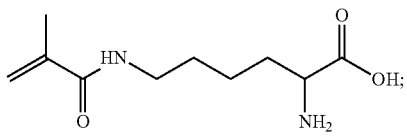

the compound having a polymerizable moiety and a functional group reactive with an amino group of repeating units derived from the second copolymerizable monomer:
is acrylic acid, (meth)acrylic acid, crotonic acid, isocrotonic acid, tiglic acid, angelic acid, or an anhydride of the aforementioned acids formed of two identical or different acids; more preferably an anhydride of the aforementioned acids formed of two identical acids; most preferably, the anhydride of acrylic acid; and
the hydrolysis-stable, water-soluble monomer having a single polymerizable double bond and a carboxylic acid group:
is itaconic acid or acrylic acid, preferably acrylic acid.

In the last mentioned particularly preferred embodiment, most preferably, the polymerizable polymer obtained in step b) has one of the following structures:

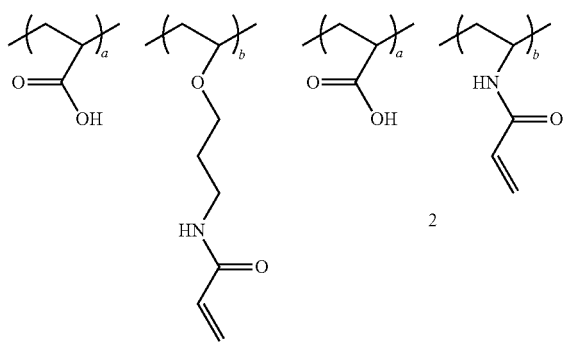

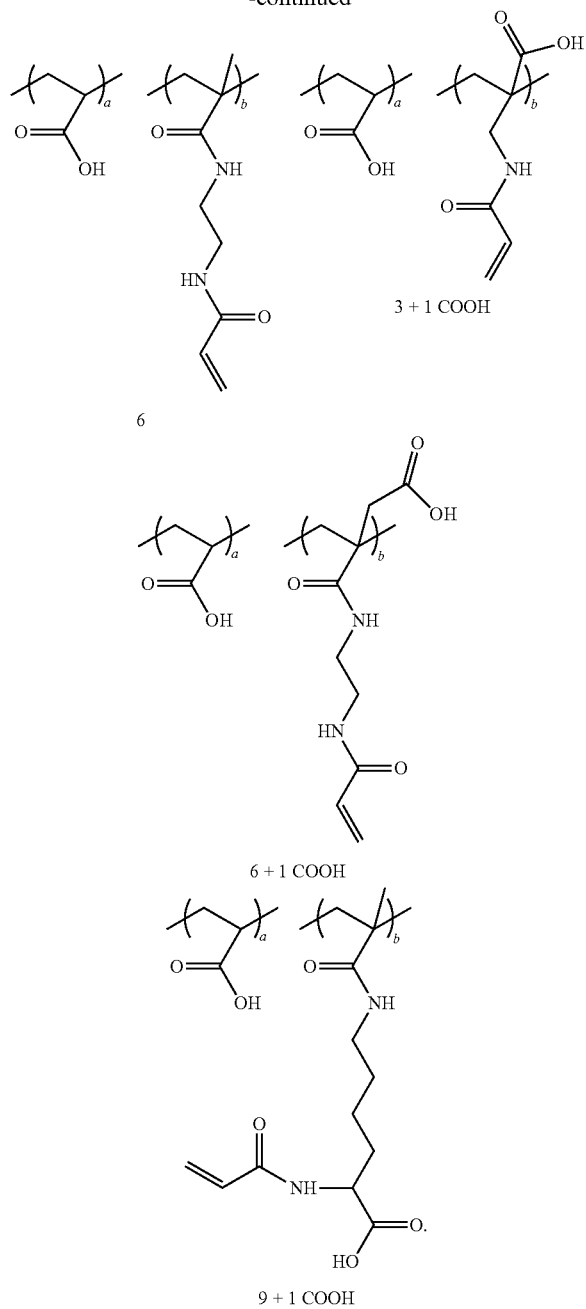

3 + 1 COOH

6

6 + 1 COOH

9 + 1 COOH

The invention will now be further illustrated by the following Examples.

EXAMPLES

In the following Examples 1 to 7, the preparation of preferred polymerizable polymers according to (B) is described. In Example 8, the preparation of aqueous dental glass ionomer compositions and the testing of the mechanical properties of cured compositions is described. Example 9 describes the measurement of tensile bond strength, and Example 10 describes the treatment of a cavitated carious lesions with a present aqueous dental glass ionomer composition as direct restoration.

Example 1

1. Copolymerisation of tert.-Butylacrylat (tButA) and 3-Aminopropylvinylether (APVE) to poly(tButA-co-APVE)

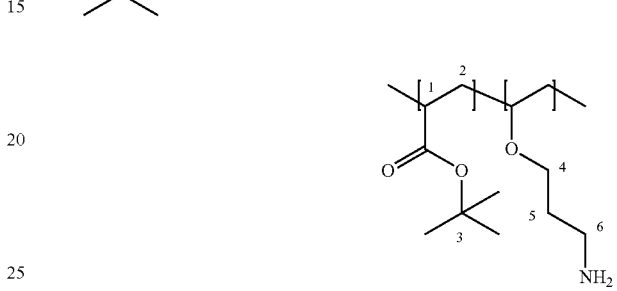

5.0 g (39 mmol) tButA, 0.99 g (9.8 mmol, 20 mol-%) APVE and 0.16 g (2 mol-%) AIBN were separately dissolved in DMF and the solutions were saturated with $N_2$. Then the solutions were combined and stirred for 24 h at 70° C. After the polymerization the cooled solution was diluted with DMF to 30 wt-% polymer solutions and precipitated in water/methanol (9:1). The separated solid was dried in vacuum.

The obtained copolymer had a molecular weight $M_n$=18 kDa, an $M_w$=51 kDa and a PD of 2.8.

IR-spectroscopy of the product showed no vinylether-vibrations while $^1$H-NMR showed broadened peaks for the aliphatic protons and no peaks for possible remaining double bond protons.

$^1$H-NMR (500 MHz, DMSO-$d_6$): δ (ppm)=3.5 (2H, 4), 2.7 (2H, 6), 2.2 (2H, 2), 1.8 (1H, 1), 1.6 (2H, 5), 1.44 (9H, 3).

2. Methacrylation of the Poly(tButA-co-APVE)

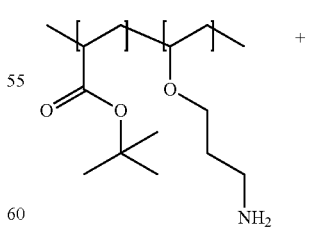

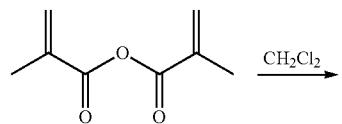

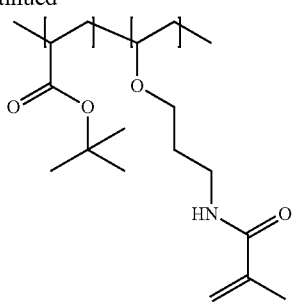

To a solution of 5 g (33.7 mmol) copolymer poly(tButA-co-APVE) dissolved in 31.5 g dichloromethane were added 1.3 g (8.42 mmol) methacrylic acid anhydride. After stirring the solution for 24 h at ambient temperature, the solvent was removed and the crude product was dissolved in 30 mL methanol. From this solution the polymer was precipitated in water, filtered off and dried in vacuum.

FT-IR: $\nu_{max}[cm^{-1}]$=2976, 2932, 1785, 1722 (Ester), 1670 (Amid I), 1626 (C=C), 1526 (Amid II), 1479, 1448, 1392, 1366, 1143, 844.

3. Hydrolysis of Ester Moieties

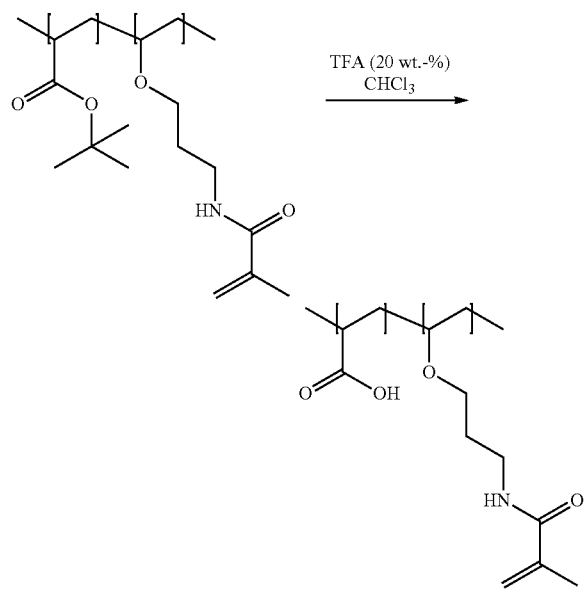

To a solution of 1.0 g (8.15 mmol) of the methacrylated poly(tButA-co-APVE) in 5 mL chloroform were added 20 wt-% trifluoro acetic acid. After stirring the solution for 5 h at 60° C. the crude precipitated polymer was separated from the solvent. The polymer was washed with chloroform, dissolved in methanol and re-precipitated in chloroform. Then the yellow polymer was dried in vacuum.

$^1$H-NMR (500 MHz, DMSO-$d_6$): δ (ppm)=12.2 (1H, —COOH), 7.8 (1H, —NH—), 5.6 (1H, —C=C—H), 5.3 (1H, C=C—H), 2.2 (2H, —CH2— backbone), 1.8 (3H, —CH$_3$), 1.8 (1H, —CH—, backbone), 1.5 (2H, O—CH$_2$CH$_2$), 1.4 (9H, C—(CH$_3$)$_3$, residual ester moieties).

Example 2

1. Copolymerization of tert butyl acrylate (t-BA) and 3-aminopropyl vinylether (APVE) to poly(AA-co-APVE)

In a three necked round bottom flask, equipped with a cooler, 2.34 mL (0.0206 mol) APVE and 8.97 mL (0.0618 mol) t-BA were mixed with 20 mL dioxane. 278 mg AIBN (2 mol-% regarding the total monomers) were dissolved, too. The reaction mixture was instantaneously flushed with Argon for about 20 min. Meanwhile a metal bath was preheated to 90° C. The polymerization was instantaneously started by placing the bath below the flask. After 1 h of stirring the reaction was complete. A sample of 5 mL was withdrawn and diluted with dioxane to 20 mL. The polymer was precipitated by adding this solution to an excess of 150 mL water. The polymer was dried at the vacuum pump. The molecular weight was determined by using SEC with DMF as eluent.

$M_n$=11500 g/mol, $M_w$=38100 g/mol, PD=3.32

2. Modification of Poly(AA-co-APVE) with Methacrylic Anhydride

To the residue of the reaction mixture from synthetic step 1 cooled down to room temperature were added 26 mg tert.-butyl hydroquinone (TBHQ) to deactivate the residual initiator. Than 0.0309 mol methacrylic anhydride were added. After stirring the mixture for 2 h at room temperature, the solvent was removed at the rotary evaporator (30° C.) and afterwards the sample was dried at the vacuum pump. The NMR-spectra shows broadened peaks at 5.30 ppm and 5.64 ppm of double bonds indicating that the modification was successful.

3. Hydrolysis of Tert.-Butyl Eater Moieties 20 g of a polymer with 5 mol-% APVE incorporated were modified with methacrylic anhydride as described above. After removing the solvents at the rotary evaporator the crude product was dissolved in 50 mL of trifluoroacetic acid. The mixture was cooled in an ice bath which was slowly dissolving and stirred for 24 h. Over night the polymer precipitated. The suspension was decanted and the polymer was dissolved in 100 mL of dioxane. It was precipitated in a fivefold excess of acetone. The precipitate was dissolved again in dioxane and precipitated again. Afterwards the polymer was first dried at the rotary evaporator and afterwards at the vacuum pump. The NMR-spectra shows that the peak of the tert-butyl group at 1.38 ppm has nearly vanished. This corresponds to a degree of hydrolysis of 98 mol-%.

Example 3

Copolymerisation of tert.-Butylacrylate and 3-Aminopropylvinylether-P(tBu-co-APVE)

A solution of 15 g (117 mmol) tert.-Butylacrylat in 38 g DMF was saturated under ice cooling with nitrogen. 3 g (29 mmol) 3-Amino-propylvinylether were added to this solution after 15 minutes. Further 5 minutes later were added 480 mg (2 mol-%) AIBN in nitrogen counter flow. Then the solution was stirred for 24 h at 70° C. After the polymerization the cooled solution was diluted with DMF to 33 wt-% polymer solutions and precipitated in the 20-fold quantity of water. The solid was filtered off, washed with water and dried in vacuum.

FT-IR: $v_{max}[cm^{-1}]$=2977 (—$CH_2$—), 1723 (ester), 1481, 1449, 1392, 1366, 1255, 1144, 845.

$^1$H-NMR (500 MHz, $CDCl_3$): δ(ppm)=3.5 (2H, —O—$CH_2$—), 2.7 (2H, —$CH_2$—$NH_2$), 2.2 (2H, backbone), 1.8 (1H, backbone), 1.6 (2H, —O—$CH_2$—$CH_2$—), 1.44 (9H, -tbutyl).

GPC (DMF): $M_n$=26 kDa, $M_w$=70 kDa, $M_z$=124 kDa, PD=2.7.

The following table shows typical molecular masses for different polymerization samples using a ratio of eq(tBA):eq(APVE)=3:1:

| Batch # | c(AIBN) [mol-%] | $t_{term.}$ [min.] | $M_n$ | $M_w$ | $M_z$ | PD |
|---|---|---|---|---|---|---|
| 044-020 | 4 | 10 | 35.600 | 81.000 | 137.000 | 2.3 |
|  |  | 30 | 40.000 | 64.200 | 94.000 | 1.6 |
|  |  | 60 | 40.400 | 60.700 | 85.100 | 1.5 |
|  |  | 1440 | 36.000 | 65.200 | 97.300 | 1.8 |
| 044-022 | 1 | 10 | 14.900 | 37.400 | 72.900 | 1.9 |
|  |  | 30 | 14.800 | 39.200 | 71.700 | 1.8 |
|  |  | 60 | 150.800 | 160.200 | 166.400 | 1.0 |
| 044-023 | 0.1 | 30 | 69.700 | 106.900 | 146.400 | 1.5 |

Itaconic Amide Modified P(tBA-co-APVE-IA)

To a clear solution of 3.0 g p(tBA-co-APVE) in 10 mL dichloro methane were added portion wise under stirring 0.4 g (3.6 mmol) itaconic acid anhydride, whereby the solution discolorates red and then yellowish. Then the solution was stirred for 24 h at room temperature prior to evaporate dichloro methane.

FT-IR: $v_{max}[cm^{-1}]$=2977 (—$CH_2$—), 1718 (ester), 1668 (amide I), 1559 (amide II), 1476, 1437, 1392, 1367, 1252, 1146, 1100, 945, 843.

Hydrolysis of Ester Moieties to P(AA-co-APVE-IA)

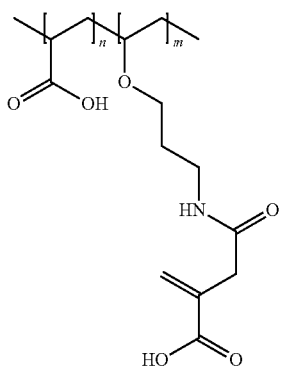

The modified polymer was added portionwise under stirring to 10 mL trifluoroacetic acid, and stirred some hours at room temperature prior to evaporate the trifluoroacetic acid in vacuum. The obtained high viscous polymer was dissolved in water and dialyzed for 4 days (MWCO=1000 g/mol). After frieze drying a reddish solid was received.

FT-IR: $v_{max}[cm^{-1}]$=3392, 2932 (—$CH_2$—), 1699 (acid), 1625 (—C=C), 1546 (amide II), 1447, 1407, 1230, 1164, 1094, 934, 798, 610

$^1$H-NMR (300 MHz, $D_2O$): δ (ppm)=8.0 (1H, —NH—), 6.4 (1H, —C=C—H), 5.6 (1H, —C=C—H), 3.5 (2H, —O—$CH_2$—), 3.4 (2H, —NH—$CH_2$—), 3.3 (2H, —NH—CO—$CH_2$—), 2.4 (1H, backbone), 2.0-1.5 (2H, backbone), 1.6 (2H, —O—$CH_2$—$CH_2$—).

Example 4

Methacrylamide Modified P(tBA-co-APVE-MA)

To a clear solution of 3.0 g p(tBA-co-APVE) of example 2 dissolved in 10 mL dichloromethane, 0.6 g (4.1 mmol) methacrylic acid anhydride was added dropwise. Then the solution was stirred for 24 h at room temperature prior to evaporation of dichloromethane. The obtained raw product was applied for further reactions without purification.

FT-IR: $v_{max}[cm^{-1}]$=3351, 2977 (—$CH_2$—), 1721 (ester), 1668 (amide I), 1622 (—C=C), 1531 (amide II), 1452, 1392, 1366, 1255, 1146, 1089, 940, 845.

Hydrolysis of Ester Moieties to P(AA-co-APVE-MA)

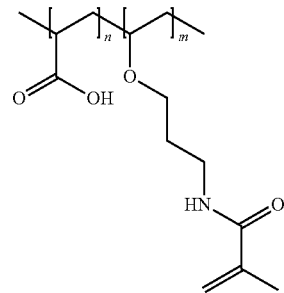

The modified polymer was added portion wise under stirring to 10 mL trifluoro acetic acid and stirred some hours at room temperature prior to evaporate the trifluoro acetic acid in vacuum. The obtained high viscous polymer was dissolved in water and dialyzed for 4 days (MWCO=1000 g/mol). After frieze drying a colorless solid was received.

FT-IR: $v_{max}[cm^{-1}]$=3180, 2934 (—$CH_2$—), 2613, 1701 (acid), 1650 (amide I), 1597, 1537 (amide II), 1449, 1408, 1211, 1162, 1110, 919, 797, 611

$^1$H-NMR (300 MHz, $D_2O$): δ (ppm)=8.0 (1H, —NH—), 5.7 (1H, —C=C—H), 5.4 (1H, —C=C—H), 3.5 (2H, —O—$CH_2$—), 3.5 (2H, —NH—$CH_2$—), 2.2 (1H, backbone), 1.8-1.6 (2H, backbone), 1.6 (2H, —O—$CH_2$—$CH_2$—).

Example 5

Acrylamide Modified P(tBA-co-APVE-AA)

To a solution of 5.0 g p(tBA-co-APVE) of example 4 dissolved in 30 mL THF were added under ice cooling drop wise 0.76 g (6.7 mmol) acryloyl chloride, whereby immediately a white solid precipitates. The reaction mixture was stirred for further 24 h at room temperature. The solid was filtered off and the solvent was evaporated. The crude raw material was used for hydrolysis without further purification.

FT-IR: $v_{max}[cm^{-1}]$=3289, 2976 (—CH—), 1722 (ester), 1659 (amide I), 1628 (—C=C), 1544 (amide II), 1480, 1448, 1366, 1254, 1143, 844.

Hydrolysis of Ester Moieties to P(AA-co-APVE-AA)

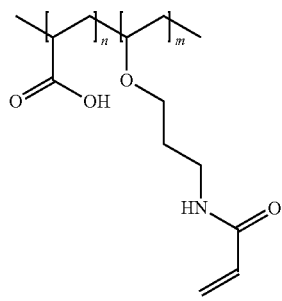

3 g of the modified polymer was added portion wise under stirring to 10 mL trifluoro acetic acid, and stirred some hours at room temperature prior to evaporate the trifluoro acetic acid in vacuum. The obtained high viscous polymer was dissolved in water and adjusted to pH 2 by addition of aqueous NaOH. Then the solution was dialyzed for 4 days (MWCO=1000 g/mol). After frieze drying a colorless solid was received.

FT-IR: $v_{max}$[cm$^{-1}$]=3361, 2930 (—CH$_2$—), 1707 (acid), 1654 (amide I), 1620 (—C=C), 1544 (amide II), 1447, 1407, 1242, 1179, 1097, 980, 801.

$^1$H-NMR (300 MHz, D$_2$O): δ (ppm)=6.3 (1H, —C=C—H), 6.2 (1H, —C=C—H), 5.8 (1H, —CH=C<), 3.6 (2H, —O—CH$_2$—), 3.3 (2H, —NH—CH$_2$—), 2.2 (1H, backbone), 1.9-1.4 (2H, backbone), 1.6 (2H, —O—CH$_2$—CH$_2$—).

Example 6

Copolymerisation of acrylic acid and N-vinyl formamide[1] to P(AA-NVFA)

N. A. Nesterova et alter, *Russian Journal of Applied Chemistry* 2008, Vol. 82, No. 4, pp. 618-621

3 g (41.6 mmol) acrylic acid and 590 mg (8.9 mmol) N-Vinylformamide were dissolved in 10.88 g distilled isopropanol and aerated with nitrogen for 30 minutes. Then 164 mg (2 mol-%) AIBN were added in the nitrogen counter flow and aerated with nitrogen for further 15 minutes. Then the solution was stirred for 24 h at 70° C., whereby a colorless solid precipitated. The solid was filtered off and washed repeatedly with acetone and dried under reduced vacuum. One obtained a colorless, fine dispersed solid.

FT-IR: $v_{max}$ [cm$^{-1}$]=3272 (—NH$_2$), 3054 (—CH$_2$—), 2922, 1708 (acid), 1643 (amide I), 1532 (amide II), 1444, 1385 (—CH$_2$—), 1244, 1178.

$^1$H-NMR (300 MHz, DMSO-d$_6$): δ (ppm)=12.2 (1H, —COOH), 7.9 (1H, —NH—COH), 4.3 (1H, —CH—NH), 2.2 (1H, —CH—COOH), 1.7 (2H, —CH$_2$—CH—NH—), 1.5 (2H, CH$_2$—CHCOOH).

GPC (H$_2$O): $M_n$=10 kDa, $M_w$=49 kDa, $M_z$=126 kDa, PD=5.0.

Conversion of P(AA-co-NVFA) Into P(AA-co-VAm)

(based on the hydrolysis of pure p(VFA) to provide p(VAm), in K. Yamamoto et alter, *Journal of Applied Polymer Science* 2002, Vol. 89, pp. 1277-1283.

200 mg of the copolymer p(AA-co-NVFA) were dissolved in 10 mL 2 N NaOH and stirred for 2 h at 100° C. Then the solution was neutralized by HCl and dialyzed for 3 days (MWCO=1000 g/mol), After freeze drying a fleece-like colorless solid was obtained.

FT-IR: $v_{max}$ [cm$^{-1}$]=3274 (—NH$_2$), 2919 (—CH2—), 1666 (—COONa), 1559 (—NH$_2$), 1448, 1408 (—CH$_2$—), 1188 (—C—O—).

$^1$H-NMR (300 MHz, D$_2$O): δ (ppm)=2.5 (1H, —CH—NH$_2$), 2.0 (1H, —CH—COOH), 1.4 (2H, —CH$_2$—CH—NH$_2$), 1.3 (2H, —CH$_2$—CH—COOH).

Acrylamide Modified P(AA-co-VAm-MA)

0.5 g of the hydrolyzed copolymer P(AA-co-VAm) were added to a round bottom flask and an excess of 1.0 g methacrylic anhydride were added. The mixture was heated to 60° C. for 4 hours. Then the product was diluted in water and the polymer was precipitated in methanol twice. The final polymer was analyzed for functionalization with double bonds by $^1$H-NMR (C=C bonds at 5.51 ppm and 5.31 ppm). The polymer is soluble in water after stirring for 24 hours. The degree of functionalization reaches 4.0 mol-%.

Example 7

Copolymerisation of Acrylic Acid and N-(2-Aminoethyl) Methacryl Amide Hydrochloride 0.2 g (3 mmol) acrylic acid and 0.5 g (3 mmol) N-(2-amino ethyl)methacryl amide hydrochloride were dissolved in 1.4 g DMF and aerated with nitrogen for 15 minutes. Then 20 mg (2 mol-%) VA-044 were added in the nitrogen counter flow and aerated with nitrogen for further 5 minutes. Then the solution was stirred for 2 h at 70° C., whereby a colorless solid precipitates. The solid was filtered off and washed repeatedly with acetone and dried under reduced vacuum. One obtained a colorless, fine dispersed solid.

FT-IR: $v_{max}$[cm$^{-1}$]=3350 (—NH$_2$), 2926, 1705 (acid), 1629 (amide I), 1527 (amide II), 1482, 1456, 1393, 1365, 1232, 1166, 837.

$^1$H-NMR (300 MHz, DMSO-d$_6$): δ (ppm)=12.3 (1H, —OH), 8.3 (1H, —NH—), 7.9 (2H, —NH$_2$), 4.2 (1H, CH3—CH<), 2.9 (2H, —NH—CH$_2$—), 2.6 (2H, —NH—CH$_2$—CH$_2$—), 1.5 (1H, backbone), 1.2 (3H, —CH$_3$), 1.0 (2H, backbone).

Example 8

Preparation and Testing of Aqueous Dental Glass Ionomer Compositions

Aqueous dental glass ionomer compositions of Examples 8A to 8H and of the Comparative Example have been prepared by forming a liquid and a powder composition of the ingredients listed in Tables 1 and 2 below, which ingredients respectively add up to 100 wt.-%.

For preparing resin modified glass ionomer (RMGI) test specimens, each liquid of Examples 8A to 8H and the Comparative Example was mixed with the respective powder in a powder/liquid (P/L) ratio indicated in Tables 1 and 2.

The resulting mixtures of powder and liquid of Examples 8A to 8H and of the Comparative Example were filled in a stainless steel mould having the size (25±2) mm×(2.0±0.1) mm×(2.0±0.1) mm, for the preparation of test specimens. The thus obtained dental glass ionomer compositions were light-cured with a dental curing light as well as self-cured, that is cured without an external power source. In Tables 1 and 2, the abbreviation "LC" means light-cured, and the abbreviation "SC" means self-cured.

For the resulting cured dental glass ionomer composition of Examples 8A to 8H, and the Comparative Example, flexural strength was determined according to ISO 4049 whereby samples were stored after irradiation for 1 h in 100% humidity at 37° C., and thereafter for 23 h in water at 37° C. taking account the nature of the material.

For comparison with the disclosure of US-A 2005/0165136, under identical measurement conditions, the flexural strength (LC) of Vitremer® light cured glass ionomer (3M Dental product) is 66±2 MPa and the flexural strength (SC) of Vitremer® light cured glass ionomer (3M Dental product) is 45±5 MPa.

The "curing time" is composed of the working time and setting time indicated in Tables 1 and 2. The terms "working time" and "setting time" are defined above in the general description.

TABLE 1

Composition of the aqueous dental glass ionomer compositions of examples 8A to 8E, curing time applied and mechanical properties of the resulting cured composition

| | | Example 8A | Example 8B | Example 8C | Example 8D | Example 8E |
|---|---|---|---|---|---|---|
| Liquid | Water | 33.2 | 33.2 | 33.2 | 33.4 | 33.1 |
| | Crosslinker | 15 | 15 | 15 | 15 | 15 |
| | Modified polyacid | 25 | 25 | 25 | 25 | 25 |
| | Acrylic acid | 24.4 | 24.4 | 24.4 | 24.5 | 24.23 |
| | Photopolymerization system (CQ) + Inhibitor (TPHQ) | 0.67 | 0.67 | 0.67 | 0.67 | 0.67 |
| | tBDA | 1.73 | 1.73 | 1.73 | — | 1.8 |
| | DMABN | — | — | — | 1.43 | 0.2 |
| | Σ | 100 | 100 | 100 | 100 | 100 |
| Powder | Reactive glass mixture | 99.3 | 99.34 | 99.4 | 99.4 | 99.3 |
| | KPS | 0.24 | 0.22 | 0.2 | 0.2 | 0.24 |
| | NapTS | 0.46 | 0.44 | 0.4 | 0.4 | 0.46 |
| | Σ | 100 | 100 | 100 | 100 | 100 |
| P/L ratio | | 2.8 | 3.0 | 3.2 | 3.2 | 2.8 |
| Curing time | Working time (seconds) | 185 | 150 | 170 | 145 | 247 |
| | Setting time (seconds) | 325 | 270 | 305 | 225 | 310 |
| | Flexural strength (SC) [MPa]/E-Modulus (SC) [MPa] | 68 ± 7/ 10700 ± 570 | 81 ± 13/ 12100 ± 300 | 97 ± 5/ 11700 ± 530 | 81 ± 8/ 11400 ± 340 | 83 ± 7/ 10000 ± 150 |
| | Flexural strength (LC) [MPa]/E-Modulus (LC) [MPa] | 109 ± 4/ 11400 ± 300 | 119 ± 15/ 12600 ± 760 | 116 ± 11/ 12400 ± 470 | 103 ± 12/ 12500 ± 200 | 111 ± 12/ 11100 ± 250 |
| | Tensile bond strength to enamel (SC) [MPa] | n.d.*) | n.d. | 22.3 ± 7 | n.d. | n.d. |
| | Tensile bond strength to enamel (LC) [MPa] | n.d. | n.d. | 19.9 ± 3.3 | n.d. | n.d. |
| | Tensile bond strength to dentine (SC) [MPa] | n.d. | n.d. | 21.2 ± 8.5 | n.d. | n.d. |
| | Tensile bond strength to dentine (LC) [MPa] | n.d. | n.d. | 28.9 ± 4.1 | n.d. | n.d. |

*)n.d.: means "not determined"

TABLE 2

Composition of the aqueous dental glass ionomer compositions of Examples 8F to 8H and the Comparative Example, curing time applied and mechanical properties of the resulting cured compositions

| | | Example 8F | Example 8G | Example 8H | Comparative Example |
|---|---|---|---|---|---|
| Liquid | Water | 33.2 | 33.2 | 34.1 | 33.8 |
| | Crosslinker | 15 | 15 | 15 | 15 |
| | Modified polyacid | 25 | 25 | 25 | — |
| | Unmodified polyacid | — | — | — | 15 |
| | Acrylic acid | 24.4 | 24.4 | 25.23 | 15 |
| | Photopolymerization system (CQ) + Inhibitor (TPHQ) | 0.67 | 0.67 | 0.67 | 0.6 |
| | tBDA | 1.73 | 1.73 | — | — |
| | DMABN | — | — | — | 0.5 |
| | Σ | 100 | 100 | 100 | 100 |
| Powder | Reactive glass mixture | 99.6 | 99.8 | 99.4 | 100 |
| | KPS | — | 0.2 | 0.2 | — |
| | NapTS | 0.4 | — | 0.4 | — |
| | Σ | 100 | 100 | 100 | 100 |
| P/L ratio | | 3.2 | 3.2 | 3.2 | 2.8 |
| Curing time | Working time (seconds) | n.d.*) | n.d. | n.d. | n.d. |
| | Setting time (seconds) | n.d. | n.d. | n.d. | n.d. |

TABLE 2-continued

Composition of the aqueous dental glass ionomer compositions of Examples 8F to 8H and the Comparative Example, curing time applied and mechanical properties of the resulting cured compositions

|  | Example 8F | Example 8G | Example 8H | Comparative Example |
|---|---|---|---|---|
| Flexural strength (SC) [MPa]/E-Modulus (SC) [MPa] | 38 ± 5/<br>6600 ± 700 | 43 ± 3/<br>9300 ± 500 | 16 ± 4/<br>4600 ± 800 | n.d. |
| Flexural strength (LC) [MPa]/ E-Modulus (LC) [MPa] | 118 ± 7/<br>12100 ± 315 | 112 ± 9/<br>12000 ± 575 | n.d. | n.d. |

*)n.d.: means "not determined"

In Tables 1 and 2, the meaning of the abbreviations for the components is as follows:
KPS: Potassium peroxodisulfate,
tBDA: tert-butyl-N,N-Dimethylaniline,
DMABN: (Dimethylamino)benzonitril, and
NapTS: Sodium para-toluenesulfinate.
unmodified PMA poly(acrylic acid-co-itaconic acid) (p(AA-co-IA)

The mechanical properties listed in Tables 1 and 2 show that the aqueous dental glass ionomer compositions of Examples 8A to 8G according to the invention all provide an advantageously high flexural strength and E-Modulus when light cured. For example 8H, high flexural strength and E-Modulus was not determined for light cured samples.

Specifically, according to Tables 1 and 2, the light cured aqueous dental glass ionomer compositions according to the present invention show a flexural strength which is up to 80% higher than the flexural strength of Vitremer® light cured glass ionomer (3M Dental product) under the test conditions used according to the present invention.

Furthermore, self-cured aqueous dental glass ionomer compositions of examples 8A to 8G impressively showed that both flexural strength and E-Modulus were significantly improved compared with the self-cured compositions of examples 8F, 8G and 8H. From Examples 8A to 8G, it appears that the specific redox initiator containing (i') potassium peroxodisulphate, (ii') tert.-butyl-N,N-dimethylaniline, and (iii') sodium para-toluenesulfinate provides for this significant improval of flexural strength and E-Modulus upon self-curing. Such excellent self-curing characteristics are highly desirable for deep carious lesions, e.g. having a depth of about 1 mm or more.

Furthermore, for the cured composition of Example 8C providing the highest flexural strength and also an excellent E-Modulus upon self-curing, additionally, tensile bond strength to enamel and dentine were determined for both self-curing and light-curing. It was surprisingly found that tensile bond strength was at least about 20 MPa and thus excellent for a reliable adhesion to the enamel or dentine.

Example 9

Measurement of the Tensile Bond Strength

Extracted teeth such as human or bovine molars are provided and may be immersed in water at a predetermined temperature for a predetermined time prior to use, for example 4° C. for 24 hrs. For having a good reproducibility, as a first model experiment, healthy teeth without (cavitated) carious lesions are used, which enamel is appropriately prepared, for example by sanding, e.g. by using wet 320 grit abrasive paper and then 600 grit abrasive paper under running water.

Then, the dental composition according to the invention is applied to the extracted teeth, for example by using the Ultradent method (ISO/TS 11406 Dental materials—Testing of adhesion to tooth structure).

Then tensile bond strength testing is carried out by using an appropriate apparatus, e.g. a Zwick test machine (Zwick Roell). A tensile load is applied till the posts debonded with a crosshead speed of 1 mm/min. The load at breaks is noted and tensile bond strength is calculated in MPa.

Example 10

Use in the Treatment of Cavitated Carious Lesions as Direct Restoration

An advanced cavitated carious lesion of Class I located at an occlusal surface of a human molar, which cavitated carious lesion has a depth of about 1 mm, is treated in-vivo. In the carious human molar, all soft and leathery dentin at the position of the carious lesion is removed by a dental drilling device, until hard dentin is reached. After drilling, the resulting cavity may have a depth of 2 mm or more. The drilled out carious lesion is cleaned by suitable means, e.g. gargling of the patient with water optionally admixed with a suitable disinfectant. The drilled out carious lesion is dried e.g. with an air stream, and then filled with the aqueous dental glass ionomer composition of Example 8C. The composition is put into shape. Finally, the shaped composition is light-cured with a suitable dental curing light such as SmartLite® Focus dental curing light (Dentsply DeTrey GmbH, Germany) with a wavelength of about 474 nm at about 1000 mW/cm$^2$ for 20 seconds for three times, to further improve the adhesion of the self-curing composition to the surface of the treated molar tooth.

The invention claimed is:
1. An aqueous dental glass ionomer composition for use in the treatment of cavitated carious lesions, wherein the glass ionomer composition comprises
   (A) a reactive particulate glass,
   (B) an hydrolysis-stable water-soluble, polymerizable polymer comprising acidic groups, which is reactive with the particulate glass in a cement reaction, whereby the polymerizable polymer has a polymer backbone and pendant groups having one or more polymerizable carbon-carbon double bonds, and
   (C) a polymerization initiator system;
   wherein component (B) does not contain an ester group which hydrolyzes in aqueous media at pH 3 at room temperature within one month, and wherein the dental glass ionomer composition, when cured, provides a permanent direct restoration having a flexural strength of at least 80 MPa.

2. The aqueous dental glass ionomer composition for use according to claim 1, wherein the carious lesions are moderate, advanced or severe carious lesions.

3. The aqueous dental glass ionomer composition for use according to claim 1, wherein the carious lesions are Class I, IV or VI carious lesions.

4. The aqueous dental glass ionomer composition for use according to claim 1, wherein the dental glass ionomer composition is a two-pack powder/liquid composition.

5. The aqueous dental glass ionomer composition for use according to claim 1, wherein the polymerization initiator system is a dual-cure initiator system containing a photoinitiator and a redox initiator.

6. The aqueous dental glass ionomer composition for use according to claim 5, wherein the redox initiator contains
(i) an inorganic peroxodisulphate salt,
(ii) an aromatic amine, and
(iii) an aromatic sulfinate salt.

7. The aqueous dental glass ionomer composition for use according to claim 6, wherein the inorganic peroxodisulphate salt is potassium peroxodisulphate.

8. The aqueous dental glass ionomer composition for use according to claim 1, wherein the cured dental glass ionomer composition provides an adhesion to enamel of at least MPa as measured according to ISO 29022:2013.

9. The aqueous dental glass ionomer composition for use according to claim 1, further comprising
(D) a hydrolysis-stable, water-soluble monomer having a single polymerizable double bond and optionally a carboxylic acid group, said monomer having a molecular weight of at most 200 Da.

10. The aqueous dental glass ionomer composition for use according to claim 1, further comprising
(E) a polymerizable hydrolysis-stable crosslinker having at least two polymerizable carbon-carbon double bonds.

11. The aqueous dental glass ionomer composition for use according to claim 1, wherein the polymerizable polymer is obtainable by a process comprising
a) a step of copolymerizing a mixture comprising
(i) a first copolymerizable monomer comprising at least one optionally protected carboxylic acid group and a first polymerizable organic moiety, and
(ii) a second copolymerizable monomer comprising one or more optionally protected primary and/or secondary amino groups and a second polymerizable organic moiety,
for obtaining an amino group containing copolymer;
b) a step of coupling to the amino group containing copolymer a compound having a polymerizable moiety and a functional group reactive with an amino group of repeating units derived from the second copolymerizable monomer in the amino group containing copolymer obtained in the first step, wherein the optionally protected amino group is deprotected, so that polymerizable pendant groups are linked to the backbone by hydrolysis-stable linking groups,
and, optionally, a step of deprotecting the protected carboxylic acid group after step a) or step b), for obtaining a polymerizable polymer.

12. The aqueous dental glass ionomer composition for use according to claim 6, wherein the aromatic amine is tert.-butyl-N,N-dimethylaniline.

13. The aqueous dental glass ionomer composition for use according to claim 6, wherein the aromatic sulfinate salt is sodium para-toluenesulfinate.

\* \* \* \* \*